US012089574B2

(12) United States Patent
Garry et al.

(10) Patent No.: US 12,089,574 B2
(45) Date of Patent: Sep. 17, 2024

(54) HUMANIZED SKELETAL MUSCLE

(71) Applicant: Regents of the University of Minnesota, Minneapolis, MN (US)

(72) Inventors: Daniel J. Garry, Eagan, MN (US); Mary G. Garry, Eagan, MN (US); Naoko Koyano, Shoreview, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 424 days.

(21) Appl. No.: 16/952,807

(22) Filed: Nov. 19, 2020

(65) Prior Publication Data
US 2021/0161110 A1 Jun. 3, 2021

Related U.S. Application Data

(62) Division of application No. 15/739,042, filed as application No. PCT/US2016/040378 on Jun. 30, 2016, now Pat. No. 10,874,092.

(60) Provisional application No. 62/187,027, filed on Jun. 30, 2015.

(51) Int. Cl.
*A01K 67/0271* (2024.01)
*A01K 67/0276* (2024.01)
*C12N 5/073* (2010.01)
*C12N 5/077* (2010.01)
*A61K 35/34* (2015.01)

(52) U.S. Cl.
CPC ...... *A01K 67/0271* (2013.01); *A01K 67/0276* (2013.01); *C12N 5/0604* (2013.01); *C12N 5/0658* (2013.01); *A01K 2217/00* (2013.01); *A01K 2217/075* (2013.01); *A01K 2217/15* (2013.01); *A01K 2227/108* (2013.01); *A01K 2267/025* (2013.01); *A61K 35/34* (2013.01); *C12N 2510/00* (2013.01); *C12N 2517/02* (2013.01)

(58) Field of Classification Search
None
See application file for complete search history.

(56) References Cited

U.S. PATENT DOCUMENTS

| 5,994,619 | A | 11/1999 | Stice et al. |
| 6,545,199 | B1 | 4/2003 | Anderson et al. |
| 8,685,737 | B2 | 4/2014 | Serber et al. |
| 9,446,076 | B2 | 9/2016 | Gaussin et al. |
| 10,874,092 | B2 | 12/2020 | Garry et al. |
| 10,897,880 | B2 | 1/2021 | Garry et al. |
| 11,673,928 | B2 | 6/2023 | Garry et al. |
| 2005/0125853 | A1 | 6/2005 | Parekh |
| 2006/0008451 | A1 | 1/2006 | Cibelli et al. |
| 2006/0191029 | A1 | 8/2006 | Gavin et al. |
| 2009/0288177 | A1 | 11/2009 | Habu et al. |
| 2010/0107263 | A1 | 4/2010 | Kerr et al. |
| 2010/0122360 | A1 | 5/2010 | Nakauchi et al. |
| 2011/0258715 | A1 | 10/2011 | Nakauchi et al. |
| 2011/0277047 | A1 | 11/2011 | Bruggemann |
| 2012/0207744 | A1 | 8/2012 | Mendlein et al. |
| 2012/0222143 | A1* | 8/2012 | Fahrenkrug ............ C12N 15/85 800/15 |
| 2014/0115728 | A1 | 4/2014 | Tector |
| 2014/0186414 | A1 | 7/2014 | Ingber et al. |
| 2015/0140658 | A1 | 5/2015 | Kamp et al. |
| 2015/0168125 | A1 | 6/2015 | Arieli et al. |
| 2016/0029604 | A1 | 2/2016 | Fahrenkrug et al. |
| 2018/0037620 | A1 | 2/2018 | Garry et al. |
| 2018/0177165 | A1 | 6/2018 | Garry et al. |

(Continued)

FOREIGN PATENT DOCUMENTS

| CN | 1212009 A | 3/1999 |
| CN | 1241210 A | 1/2000 |

(Continued)

OTHER PUBLICATIONS

Francetic and Li. Transcription 2-3, 109-114; May/Jun. 2011 (Year: 2011).*
"U.S. Appl. No. 15/554,585, Final Office Action mailed Aug. 2, 2019", 28 pgs.
"U.S. Appl. No. 15/554,585, Non Final Office Action mailed Jun. 1, 2020", 36 pgs.
"U.S. Appl. No. 15/554,585, Preliminary Amendment filed Aug. 30, 2017", 7 pgs.
"U.S. Appl. No. 15/554,585, Response filed Feb. 3, 2020 to Final Office Action mailed Aug. 2, 2019", 11 pgs.
"U.S. Appl. No. 15/554,585, Response filed May 7, 2019 to Non Final Office Action mailed Nov. 7, 2018", 18 pgs.

(Continued)

*Primary Examiner* — Marcia S Noble
(74) *Attorney, Agent, or Firm* — Schwegman Lundberg & Woessner, P.A.

(57) ABSTRACT

Described herein is a method for producing a chimeric non-human animal expressing a human a MYF5, MYOD, MRF4 gene or a combination thereof gene comprising: a) generating an MYF5, MYOD, MRF4 or combination thereof null non-human animal cell, wherein both copies of the non-human MYF5, MYOD, MRF4 gene or combination thereof carry a mutation that prevents production of functional MYF5, MYOD, MRF4 protein or combination thereof in said non-human animal; b) creating a MYF5, MYOD, MRF4 or combination thereof null non-human blastocyst by somatic cell nuclear transfer comprising fusing a nucleus from said MYF5, MYOD, MRF4 or combination thereof null non-human animal cell of a) into an enucleated non-human oocyte and activating said oocyte to divide so as to form an MYF5, MYOD, MRF4 or combination thereof null non-human blastocyst; c) introducing human stem cells into the MYF5, MYOD, MRF4 or combination null non-human blastocyst of b); and d) implanting said blastocyst from c) into a pseudopregnant surrogate non-human animal to generate a chimeric non-human animal expressing human MYF5, MYOD, MRF4 or combination thereof.

3 Claims, 8 Drawing Sheets
Specification includes a Sequence Listing.

(56) References Cited

U.S. PATENT DOCUMENTS

| | | | |
|---|---|---|---|
| 2018/0177166 | A1 | 6/2018 | Garry et al. |
| 2019/0133093 | A1 | 5/2019 | Nakauchi et al. |
| 2021/0169054 | A1 | 6/2021 | Garry et al. |
| 2023/0365638 | A1 | 11/2023 | Garry et al. |

FOREIGN PATENT DOCUMENTS

| | | | |
|---|---|---|---|
| CN | 102196722 | A | 9/2011 |
| CN | 102438636 | A | 5/2012 |
| CN | 108024522 | A | 5/2018 |
| CN | 108125943 | A | 6/2018 |
| CN | 108472318 | A | 8/2018 |
| EP | 2258166 | A1 | 12/2010 |
| GB | 2475656 | A | 5/2011 |
| JP | 2010515737 | A | 5/2010 |
| JP | 2014533491 | A | 12/2014 |
| JP | 2018506984 | A | 3/2018 |
| JP | 2018-522553 | A | 8/2018 |
| JP | 2018-523999 | A | 8/2018 |
| WO | WO-2004004447 | A2 | 1/2004 |
| WO | WO-2008102602 | A1 | 8/2008 |
| WO | WO-2009104794 | A1 | 8/2009 |
| WO | WO-2015168125 | A1 | 11/2015 |
| WO | WO-2016141234 | A1 | 9/2016 |
| WO | WO-2017004367 | A1 | 1/2017 |
| WO | WO-2017004388 | A1 | 1/2017 |
| WO | WO-2017075276 | A2 | 5/2017 |

OTHER PUBLICATIONS

"U.S. Appl. No. 15/554,585, Supplemental Preliminary Amendment filed Sep. 12, 2017", 3 pgs.
"U.S. Appl. No. 15/739,042, Non Final Office Action mailed Apr. 1, 2020", 27 pgs.
"U.S. Appl. No. 15/739,042, Notice of Allowance mailed Aug. 19, 2020", 10 pgs.
"U.S. Appl. No. 15/739,042, Preliminary Amendment filed Dec. 21, 2017", 9 pgs.
"U.S. Appl. No. 15/739,042, Response filed Mar. 9, 2020 to Restriction Requirement mailed Jan. 8, 2020", 11 pgs.
"U.S. Appl. No. 15/739,042, Response filed Jun. 12, 2020 to Non Final Office Action mailed Apr. 1, 2020", 12 pgs.
"U.S. Appl. No. 15/739,042, Restriction Requirement mailed Jan. 8, 2020", 10 pgs.
"U.S. Appl. No. 15/739,066, Non Final Office Action mailed Apr. 1, 2020", 24 pgs.
"U.S. Appl. No. 15/739,066, Response filed Feb. 28, 2020 to Restriction Requirement mailed Dec. 31, 2019", 11 pgs.
"U.S. Appl. No. 15/739,066, Response filed Jun. 30, 2020 to Non Final Office Action mailed Apr. 1, 2020", 11 pgs.
"U.S. Appl. No. 15/739,066, Restriction Requirement mailed Dec. 31, 2019", 10 pgs.
"U.S. Appl. No. 15/739,066, Preliminary Amendment filed Dec. 21, 2017", 9 pgs.
"Australian Application Serial No. 2016288196, First Statement of Proposed Amendments filed Jan. 31, 2018", 12 pgs.
"Canadian Application Serial No. 2,978,457, Voluntary Amendment filed Oct. 19, 2018", 10 pgs.
"Canadian Application Serial No. 2,991,053, Voluntary Amendment filed Oct. 18, 2018", 13 pgs.
"Colombian Application Serial No. NC2018/0000859, Office Action mailed Feb. 21, 2018", (w/ English Translation), 6 pgs.
"Colombian Application Serial No. NC2018/0000859, Response filed Jun. 13, 2018 to Office Action mailed Feb. 21, 2018", (w/ English Translation of Claims), 14 pgs.
"Directive 98/44/EC of the European Parliament and of the Council of Jul. 6, 1998", Official Journal of the European Communities, (1998), 9 pgs.
"Egyptian Application Serial No. PCT 1471/2017, Office Action mailed Aug. 22, 2019", (w/ English Summary), 4 pgs.

"European Application Serial No. 16759528.9, Communication Pursuant to Article 94(3) EPC mailed Nov. 22, 2019", 6 pgs.
"European Application Serial No. 16759528.9, Extended European Search Report mailed Aug. 8, 2018", 8 pgs.
"European Application Serial No. 16759528.9, Response filed Mar. 20, 2020 to Communication Pursuant to Article 94(3) EPC mailed Nov. 22, 2019", 25 pgs.
"European Application Serial No. 16759528.9, Response filed Jun. 5, 2019 to Communication dated Apr. 8, 2019 and to the Supplemental European Search Report", 11 pgs.
"European Application Serial No. 16818799.5, Communication Pursuant to Article 94(3) EPC mailed Jun. 12, 2020", 5 pgs.
"European Application Serial No. 16818799.5, Extended European Search Report mailed Feb. 28, 2019", 10 pgs.
"European Application Serial No. 16860825.5, Supplementary European Search Report mailed Apr. 9, 2019", 12 pgs.
"European Application Serial No. 16860830.5, Supplementary Partial European Search Report mailed Apr. 16, 2019", 13 pgs.
"European Application Serial No. 16818785.4, Extended European Search Report mailed Jan. 24, 2019", 7 pgs.
"European Application Serial No. 16818785.4, Response filed May 21, 2018 to Office Action mailed Feb. 16, 2018", 5 pgs.
"European Application Serial No. 16818785.4, Response filed Aug. 9, 2019 to Extended European Search Report mailed Jan. 24, 2019", 6 pgs.
"European Application Serial No. 16818799.5, Response filed May 21, 2018 to Office Action mailed Feb. 16, 2018", 5 pgs.
"International Application Serial No. PCT/US16/20768, International Search Report mailed Jul. 22, 2016", 3 pgs.
"International Application Serial No. PCT/US16/20768, Written Opinion mailed Jul. 22, 2016", 4 pgs.
"International Application Serial No. PCT/US2016/020768, International Preliminary Report on Patentability mailed Sep. 14, 2017", 6 pgs.
"International Application Serial No. PCT/US2016/040378, International Preliminary Report on Patentability mailed Jan. 11, 2018", 9 pgs.
"International Application Serial No. PCT/US2016/040378, International Search Report mailed Oct. 26, 2016", 4 pgs.
"International Application Serial No. PCT/US2016/040378, Written Opinion mailed Oct. 26, 2016", 7 pgs.
"International Application Serial No. PCT/US2016/040431, International Preliminary Report on Patentability mailed Jan. 11, 2018", 9 pgs.
"International Application Serial No. PCT/US2016/040431, International Search Report mailed Oct. 26, 2016", 4 pgs.
"International Application Serial No. PCT/US2016/040431, Written Opinion mailed Oct. 26, 2016", 7 pgs.
"Japan Approves First Human-Animal Embryo Experiments", Retrieved from the Internet: URL:<https://www.nature.com/articles/d41586-019-02275-3> [retrieved on Nov. 19, 2019], (Jul. 26, 2019).
"Japanese Application Serial No. 2017-546061, Notification of Reasons for Refusal mailed Jan. 15, 2020", (w/ English Translation), 12 pgs.
"Japanese Application Serial No. 2017-546061, Written Amendment filed Dec. 1, 2017", (w/ English Translation of Amended Claims), 11 pgs.
"Japanese Application Serial No. 2017-568252, Notification of Reasons for Rejection mailed Jun. 29, 2020", 12 pgs.
"Japanese Application Serial No. 2017-568279, Notification of Reasons for Rejection mailed Apr. 6, 2020", w/ English Translation, 8 pgs.
"New Zealand Patent Application Serial No. 735956, Voluntary Amendment filed Oct. 31, 2017", 45 pgs.
"Singaporean Patent Application No. 11201707151Y, Response filed Jan. 7, 2019 to Search Report and Written Opinion mailed Aug. 6, 2018", (w/ English Claims), 42 pgs.
"Singaporean Patent Application No. 11201707151Y, Search Report and Written Opinion mailed Aug. 6, 2018", 12 pgs.
"Vietnamese Application Serial No. 1-2017-03882, Office Action mailed Dec. 4, 2017", (w/ English Translation), 2 pgs.

(56) References Cited

OTHER PUBLICATIONS

"Vietnamese Application Serial No. 1-2017-03882, Response filed Jan. 4, 2018 to Office Action mailed Dec. 4, 2017", (w English Translation of Amended Claims), 9 pgs.

Beaucage, S. L., et al., "Deoxynucleoside Phosphoramidites—A New Class of Key Intermediate for Deoxypolynucleotide Synthesis", Tetrahedron Letters, 22, (1981), 1859-1862.

Berkes, C. A., et al., "MyoD and the transcriptional control of myogenesis", Seminars in Cell & Developmental Biology, 16, (2005), 585-595.

Bodmer, R., "The gene tinman is required for specification of the heart and visceral muscles in *Drosophila*", Development, 118(3), (1993), 719-729.

Bort, R., et al., "Hex homeobox gene controls the transition of the endoderm to a pseudostratified, cell emergent epithelium for liver bud development", Developmental Biology, 290(1), (2006), 44-56.

Bouchard, Maxime, et al., "Nephric lineage specification by Pax2 and Pax8", Genes & Development, 16(22), (2002), 2958-2970.

Bowlin, K. M., et al., "Kbtbd5 is regulated by MyoD and restricted to the myogenic lineage", Differentiation, 86, (2013), 184-191.

Bruneau, B. G., et al., "A Murine Model of Holt-Oram Syndrome Defines Roles of the T-Box Transcription Factor Tbx5 in Cardiogenesis and Disease", Cell, 106(6), (Sep. 21, 2001), 709-721 pgs.

Caprioli, A., et al., "Nkx2-5 Represses Gata1 Gene Expression and Modulates the Cellular Fate of Cardiac Progenitors During Embryogenesis", Circulation, 123(15), (2011), 1633-1641.

Carlson, D. F., et al., "Efficient TALEN-mediated gene knockout in liverstock", Proc. Natl. Acad. Sci., 109(43), (2012), 17382-17387.

Cui, et al., "Gene targeting by TALEN-induced homologous recombination in goats directs production of β-lactoglobulin-free, high-human lactoferrin milk", Scientific Reports 5:10482. DIO: 10.1038/srep10482, (May 2015), 1-11.

Elcheva, Irina, et al., "Direct induction of hematoendothelial programs in human pluripotent stem cells by transcriptional regulators", Nature Communications, 5: 5372, (2014), 1-11.

Ferdous, A., et al., "Nkx2-5 transactivates the Ets-related protein 71 gene and specifies an endothelial/endocardial fate in the developing embryo", Proc. Natl. Acad. Sci. USA, 106(3), (2009), 814-819.

Garry, D. J., et al., "A Common Progenitor at the Heart of Development", Cell, 127(6), (2006), 1101-1104.

Garry, D. J., et al., "Cardiac Regeneration—Self-Service at the Pump", Circulation Research, 95, (2004), 852-854.

Goto, Teppei, et al., "Generation of pluripotent stem cell-derived mouse kidneys in Sall1-targeted anephric rats", Nature Communications, 10, Article No. 451, (2019), 1-9.

Grefte S., Kuijpers Mar, et al., "Myogenic capacity of muscle progenitor cells from head and limb muscles", Eur. J. Oral Sci., 120(1), (2012), 38-45.

Hiroi, Y., "Tbx5 associates with Nkx2-5 and synergistically promotes cardiomyocyte differentiation", Nat Genet., 28(3), (2001), 276-280.

Jansen, K. M., et al., "Molecular Control of Mammalian Myoblast Fusion", Methods in Molecular Biology, vol. 475—Cell Fusion: Overviews and Methods, (Feb. 2008), 115-133.

Kassar-Duchossoy, L., et al., "Mrf4 determines skeletal muscle identity in Myf5:Myod double-mutant mice", Nature, 4317007), (2004), 466-471.

Kassar-Duchossoy, L., et al., "Mrf4 Determines Skeletal Muscle Identity in Myf5:Myod Double-Mutant Mice", Nature, 431, (2004), 466-471.

King, T. J., et al., "Embryo development and establishment of pregnancy after embryo transfer in pigs: Coping with limitations in the availability of viable embryos", Reproduction, 123(4), (2002), 507-515.

Kobayashi, Toshihiro, et al., "Generation of Rat Pancreas in Mouse by Interspeci?c Blastocyst Injection of Pluripotent Stem Cells", Cell, 142(5), (Sep. 1, 2010), 787-799 pgs.

Koyano-Nakagawa, N., et al., "Feedback Mechanisms Regulate Ets Variant 2 (Etv2) Gene Expression and Hematoendothelial Lineages", J. Biol. Chem., 290(40), (2015), 28107-28119.

Koyano-Nakagawa, Naoko, et al., "Etv2 is expressed in the yolk sac hematopoietic and endothelial progenitors and regulates Lmo2 gene expression", Stem Cells, 30(8), (2012), 1611-1623.

Kure-Bayashi, S., et al., "Successful implantation of in vitro-matured, electo-activated oocytes in the pig", Theriogenology, 53(5), (2000), 1105-1119.

Lammerts Van Bueren, Kelly, et al., "Regulation of endothelial and hematopoietic development by the ETS transcription factor Etv2", Current Opinion in Hematology, 19(3), (Mar. 2012), 199-205.

Latif, S., et al., "Transcriptional Pathways Direct Cardiac Development and Regeneration", Trends Cardiovasc Med., 16(7), (2006), 234-240.

Lewis, F. C., et al., "Porcine Sketal Muscke-Derived Multipotent PW1pos/Pax7neg Interstitial cells: Isolation, Characterization, and Long-Term Culture", Stem Cells Transl Med, 3(6), (2014), 702-712.

Lillico, Simon G., et al., "Live pigs produced from genome edited zygotes", Scientific Reports, 3: 2847, (2013), 1-4.

Liu, Yunying, et al., "Generation of functional organs from stem cells", Cell Regeneration, 2:1, (2013), 1-6.

Lyons, Ian, et al., "Myogenic and morphogenetic defects in the heart tubes of murine embryos lacking the homeo box gene Nkx2-5", Genes & Development, 9(13), (1995), 1654-1666.

Matsunari, Hitomi, et al., "Blastocyst complementation generates exogenic pancreas in vivo in apancreatic cloned pigs", Proc. Natl. Acad. Sci., 110(12), (Feb. 19, 2013), 4557-4562 pgs.

Matsunari, Hitomi, et al., "Blastocyst complementation generates exogenic pancreas in vivo in apancreatic cloned pigs", Proc. Natl. Acad. Sci., USA, 110(12), (May 30, 2018), 4557-4562.

Matteucci, M. D., et al., "Synthesis of Deoxyoligonucleotides on a Polymer Support", J. Am. Chem. Soc., 103, (1981), 3185-3191.

Mckarney, Lesley A., et al., "Myogenesls in Cultures of Uniparental Mouse Embryonic Stem Cells: Differing Patterns of Expression of Myogenic Regulatory Factors", Int. J. Dev. Biol., 41, (1997), 485-490.

Morita, Rimpei, et al., "ETS transcription factor ETV2 directly converts human fibroblasts into functional endothelial cells", Proceedings of the National Academy of Sciences, 112,(1), (Dec. 24, 2014), 160-165.

Nagashima, Hiroshi, et al., "Growing human organs in pigs—A dream or reality?", Theriogenology, 86(1), (2016), 422-426.

Nakano, Kazuaki, et al., "Generating Porcine Chimeras Using Inner Cell Mass Cells and Parthenogenetic Preimplantation Embryos", PLoS One, 8(4): e61900, (Apr. 2013), 1-10.

Niu, Yuyu, et al., "Generation of Gene-Modified Cynomolgus Monkey via Cas9/RNA-Mediated Gene Targeting in One-Cell Embryos", Cell 156, (Feb. 2014), 836-843.

Ott, M.-O., et al., "Early Expression of the Myogenic Regulatory Gene, myf-5, in Precursor Cells of Skeletal Muscle in the Mouse Embryo", Development, 111(4), (1991), 1097-1107.

Pasut, A., et al., "Chapter 3—Isolation of Muscle Stem Cells by Fluorescence Activated Cell Sorting Cytometry", DiMario, J. X., (ed.), Myogenesis: Methods Mol Biol., vol. 798, (2012), 53-64.

Rashid, Tamir, et al., "Revisiting the Flight of Icarus: Making Human Organs from PSCs with Large Animal Chimeras", Cell Stem Cell 15, (Oct. 2014), 406-409.

Rasmussen, T. L., et al., "Abstract 15450: Ets Related Protein 71 Regulates Cardiac Morphogenesis", Circulation, 122: A15450, (2010), 2 pgs.

Rasmussen, T. L., et al., "ER71 directs mesodermal fate decisions during embryogenesis", Development 138, (2011), 4801-4812.

Rasmussen, T. L., et al., "Getting to the Heart of Myocardial Stem Cells and Cell Therapy", Circulation, 123, (2011), 1771-1779.

Rasmussen, Tara L., et al., "Abstract 17036: Flk1 Mediated Activation of ER71 and Specification of Cardiovascular Lineages", Circulation, 124: A17036, (2011), 2 pgs.

Rasmussen, Tara L., et al., "Etv2 rescues Flk1 mutant embryoid bodies", Genesis, 51(7), (2013), 471-480.

Rasmussen, Tara L., et al., "VEGF/Flk1 Signaling Cascade Transactivates Etv2 Gene Expression", PLoS One, 7(11): e50103, (Nov. 2012), 1-12.

Rudnicki, Michael A., et al., "MyoD or Myf-5 is required for the formation of skeletal muscle", Cell 75(7), (1993), 1351-1359.

(56) References Cited

OTHER PUBLICATIONS

Sabourin, L. A., et al., "The molecular regulation of myogenesis", Clin. Genet., 57, (2000), 16-25.
Shi, X., et al., "Cooperative interaction of Etv2 and Gata2 regulates the development of endothelial and hematopoietic lineages", Developmental Biology, 389(2), (2014), 208-218.
Shi, X., et al., "Muscle stem cells in development, regeneration, and disease", Genes & Development 20, (2006), 1692-1708.
Shi, Xiaozhong, et al., "The Transcription Factor Mespl Interacts with CAMP-responsive Element Binding Protein 1 (Crebl) and Coactivates Ets Variant 2 (Etv2) Gene Expression", The Journal of Biological Chemistry, 290(15), (Feb. 18, 2015), 9614-9625.
Srivastava, D., et al., "Regulation of cardiac mesodermal and neural crest development by the bHLH transcription factor", Nat Gen., 16(2), (1997), 154-160.
Swaminathan, Preethi, "Human Stem Cell Complementation in PITX3 Null Porcine Blastocysts: Lens Development", Thesis, University of Minnesota, in partial fulfillment of the requirements of Master of Science, [Online]. Retrieved from the Internet: <https://conservancy.unm.edu/bi tstream/handle/11299/185108/Swaminathan_umn_0130M_15713.pdf>, (Dec. 2014), 57 pages.
Takeda, Kumiko, "Microinjection of serum-starved mitochondria derived from somatic cells affects parthenogenetic development of bovine and murine oocytes", Mitochondrion, 10(2), (Mar. 2010), 137-142.
Tan, Wenfang, et al., "Efficient nonmeiotic allele introgression in livestock using custom endonucleases", Proc. Natl. Acad. Sci., 110(41), (2013), 16526-16531.
Tapscott, Stephen J., et al., "The circuitry of a master switch: Myod and the regulation of skeletal muscle gene transcription", Development, 132(12), (2005), 2685-2695.
Te Pas, M. F., et al., "Biochemical pathways analysis of microarry results: regulation of myogenesis in pigs", BMC Dev. Bio., 7: 66, (2007), 1-15.
Usui, Jo-Ichi, et al., "Generation of Kidney from Pluripotent Stem Cells via Blastocyst Complementation", The American Journal of Pathology, 180(6), (Jun. 2012), 2417-2426.
Valdez, M. Renee, et al., "Failure of Myf5 to Support Myogenic Differentiation without Myogenin, MyoD, and MRF4", Developmental Biology, 219(2), (2000), 287-298.
Wang, Haoyi, et al., "One-Step Generation of Mice Carrying Mutations in Multiple Genes by CRISPR/Cas-Mediated Genome Engineering", Cell, 153, (2013), 910-918.
Wang, Xianlong, et al., "Efficient CRISPR/Cas9-mediated biallelic gene disruption and site-specific knockin after rapid selection of highly active sgRNAs in pigs", Scientific Reports, 5: 13348, (2015), 1-11.
Wareing, Sarah, et al., "The Flk1-Cre-Mediated Deletion of ETV2 Defines Its Narrow Temporal Requirement During Embryonic Hematopoietic Development", Stem Cells, vol. 30, (Jul. 18, 2012), 1521-1531.
Woolf, A. D., et al., "Burden of major musculoskeletal conditions", Bulletin of the World Health Organization, 81(9), (2003), 646-656.
Wu, et al., "TALE nickase-mediated SP110 knockin endows cattle with increased resistance to tuberculosis", PNAS, <www.pnas.org/cgi/doi/10.1073/pnas>, (Mar. 2015), E1530-E1539.
Wu, J., et al., "Generation of human organs in pigs via interspecies blastocyst complementation", Reprod Dom Anim 51(Suppl. 2), (2016), 18-24.
Wu, Jun, et al., "An alternative pluripotent state confers interspecies chimaeric competency", Nature, vol. 521, (2015), 23 pgs.
Wu, Jun, et al., "Interspecies Chimerism with Mammalian Pluripotent Stem Cells", Cell, 168(3), (2017), 473-486 (30 pgs.).
Yamagishi, H., "The combinatorial activities of Nkx2.5 and dHAND are essential for cardiac ventricle formation", Developmental Biology, 239(2), (Nov. 15, 2001), 190-203.
Yao, et al., "Efficient bi-allelic gene knockout and site-specific knock-in mediated by TALENs in pigs", Scientific Reports 4:6926, DIO: 10.1038/srep06926, (2014), 1-8.

Zhou, Bin, et al., "Nkx2-5- and Isl1-expressing cardiac progenitors contribute to proepicardium", Biochemical and Biophysical Research Communications, 375(3), (2008), 450-453.
Zhou, Lei, et al., "Cardiac Gene Activation Analysis in Mammalian Non-Myoblasic Cells by Nkx2-5, Tbx5, Gata4 and Myocd", PLOS ONE 7(6): e48028-e48028, (Oct. 2012), 1-12.
Zhou, Xiaoqing, et al., "Generation of CRISPR/Cas9-mediated gene-targeted pigs via somatic cell nuclear transfer", Cell. Mol. Life Sci., 72, (2015), 1175-1184.
Zhu, J., "In Vitro and In Vivo Developmental Competence of Ovuated and In Vitro Matured Porcine Oocytes Activated by Electrical Activation", Cloning Stem Cells, 5(4), (2003), 355-365.
"U.S. Appl. No. 15/554,585, Final Office Action mailed Apr. 19, 2021", 26 pgs.
"U.S. Appl. No. 15/554,585, Final Office Action mailed Jul. 1, 2022", 23 pgs.
"U.S. Appl. No. 15/554,585, Non Final Office Action mailed Oct. 26, 2021", 20 pgs.
"U.S. Appl. No. 15/554,585, Response filed Apr. 26, 2022 to Non Final Office Action mailed Oct. 26, 2021", 7 pgs.
"U.S. Appl. No. 15/554,585, Response filed Sep. 20, 2021 to Final Office Action mailed Apr. 19, 2021", 9 pgs.
"U.S. Appl. No. 15/554,585, Response filed Dec. 27, 2022 to Final Office Action mailed Jul. 1, 2022", 4 pgs.
"U.S. Appl. No. 17/118,981, Supplemental Preliminary Amendment filed Feb. 22, 2021", 7 pgs.
"Canadian Application Serial No. 2,978,457, Commissioner's Notice—Request for Examination Not Made mailed Mar. 24, 2021", 1 pg.
"Canadian Application Serial No. 2,991,053, Commissioner's Notice mailed Jul. 21, 2021", 1 pg.
"Canadian Application Serial No. 2,991,056, Commissioner's Notice mailed Jul. 21, 2021", 1 pg.
"Chinese Application Serial No. 201680024200.8, Decision of Rejection mailed Dec. 23, 2021", (w/ English Translation), 8 pgs.
"Chinese Application Serial No. 201680024200.8, Office Action mailed Jul. 16, 2021", (w/ English Translation), 10 pgs.
"Chinese Application Serial No. 201680024200.8, Response filed Nov. 30, 2021 to Office Action mailed Jul. 16, 2021", (w/ English Translation of Claims), 13 pgs.
"Chinese Application Serial No. 201680049673.3, Decision of Rejection mailed Feb. 22, 2022", (w/ English Translation), 12 pgs.
"Chinese Application Serial No. 201680049673.3, Office Action mailed Jan. 5, 2021", (w/ English Translation), 20 pgs.
"Chinese Application Serial No. 201680049673.3, Office Action mailed Sep. 6, 2021", (w/ English Translation), 10 pgs.
"Chinese Application Serial No. 201680049673.3, Response filed Jan. 4, 2022 to Office Action mailed Sep. 6, 2021", (w/ English Translation of Claims), 15 pgs.
"Chinese Application Serial No. 201680049673.3, Response filed May 20, 2021 to Office Action mailed Jan. 5, 2021", (w/ English Translation), 23 pgs.
"Chinese Application Serial No. 201680050242.9, Decision of Rejection mailed Jan. 24, 2022", (w/ English Translation), 11 pgs.
"Chinese Application Serial No. 201680050242.9, Office Action mailed Jan. 12, 2021", (w/ English Translation), 13 pgs.
"Chinese Application Serial No. 201680050242.9, Office Action mailed Jul. 30, 2021", (w/ English Translation), 15 pgs.
"Chinese Application Serial No. 201680050242.9, Response filed May 12, 2021 to Office Action mailed Jan. 12, 2021", (w/ English Translation), 18 pgs.
"Chinese Application Serial No. 201680050242.9, Response filed Dec. 14, 2021 to Office Action mailed Jul. 30, 2021", (w/ English Translation of Claims), 6 pgs.
"European Application Serial No. 16759528.9, EPO Written Decision to Refuse mailed Feb. 11, 2022", 22 pgs.
"European Application Serial No. 16759528.9, Grounds of Appeal filed Jun. 13, 2022", 9 pgs.
"European Application Serial No. 16759528.9, Notice of Appeal filed Apr. 7, 2022 to EPO Written Decision to Refuse mailed Feb. 11, 2022", 1 pg.
"European Application Serial No. 16759528.9, Response filed Nov. 5, 2021 to Summons to Attend Oral Proceedings mailed Mar. 12, 2021", 46 pgs.

(56) References Cited

OTHER PUBLICATIONS

"European Application Serial No. 16759528.9, Summons to Attend Oral Proceedings mailed Mar. 12, 2021", 9 pgs.
"European Application Serial No. 16818785.4, Response filed Feb. 5, 2021 to Communication Pursuant to Article 94(3) EPC Aug. 20, 2020", 11 pgs.
"European Application Serial No. 16818799.5, Communication Pursuant to Article 94(3) EPC mailed Apr. 13, 2022", 5 pgs.
"European Application Serial No. 16818799.5, Response filed Sep. 29, 2022 to Communication Pursuant to Article 94(3) EPC mailed Apr. 13, 2022", Claims not amended in response filed, 10 pgs.
"Korean Application Serial No. 10-2017-7027376, Voluntary Amendment Filed Feb. 16, 2021", (w/ English Translation of Claims), 11 pgs.
"Mexican Application Serial No. MX/a/2017/011345, Office Action mailed Sep. 3, 2021", (w/ English Translation), 10 pgs.
Das, S., et al., "Generation of human endothelium in pig embryos deficient in ETV2", (w/ Supplementary Information), *Nature Biotechnology*, 38(3), (2020), 31 pgs.
Hashimoto, Haruo, et al., "Development of Blastocyst Complementation Technology Without Contributions to Gametes and the Brain", *Experimental Animals, vol. 68, No. 3*, Retrieved from the Internet: <URL:https://www.ncbi.nlm.nih.gov/pmc/articles/PMC6699975/pdf/expanim-68-361.pdf>, (Jan. 1, 2019), 361-370.
"U.S. Appl. No. 15/554,585, Non-Final Office Action mailed Nov. 7, 2018", 19 pgs.
"U.S. Appl. No. 15/554,585, Response filed Feb. 4, 2021 to Non-Final Office Action mailed Jun. 1, 2020", 10 pgs.
"U.S. Appl. No. 15/739,066, Notice of Allowance mailed Sep. 18, 2020", 10 pgs.
"U.S. Appl. No. 17/118,981, Preliminary Amendment filed Dec. 11, 2020", 9 pgs.
"Chinese Application Serial No. 201680024200.8, Office Action mailed Jun. 15, 2020", (w/ English Translation), 9 pgs.
"Chinese Application Serial No. 201680024200.8, Response filed Dec. 29, 2020 to Office Action mailed Jun. 15, 2020", (w/ English Translation of Claims), 25 pgs.
"Chinese Application Serial No. 201680049673.3, Office Action mailed Jan. 5, 2021", (w/ Concise Statement of Relevance), 11 pgs.
"Chinese Application Serial No. 201680050242.9, Office Action mailed Jan. 12, 2021", (w/ Concise Statement of Relevance), 9 pgs.
"European Application Serial No. 16818785.4, Communication Pursuant to Article 94(3) EPC Aug. 20, 2020", 4 pgs.
"European Application Serial No. 16818799.5, Response filed Dec. 11, 2020 to Communication Pursuant to Article 94(3) EPC mailed Jun. 12, 2020", 11 pgs.
"Japanese Application Serial No. 2017-546061, Examiners Decision of Final Refusal mailed Oct. 1, 2020", 2 pgs.
Ifkovits, Jamie L., et al., "Inhibition of TGFb Signaling Increases Direct Conversion of Fibroblasts to Induced Cardiomyocytes", PLoSONE, 9(2): e89678, (Feb. 2014), 1-11.
Kataoka, Hiroshi, et al., "Etv2/ER71 induces vascular mesoderm from Flk1+PDGFR alpha+ primitive mesoderm", Blood, 18(26), (2011), 6975-6986.

Mckarney, L. A., et al., "Myogenesis in Cultures of Uniparental Mouse Embryonic Stem Cells: Differing Patterns of Expression of Myogenic Regulatory Factors", Int. J. Dev. Biol., 41, (1997), 485-490.
Wareing, S., et al., "The Flk1-Cre-Mediated Deletion of ETV2 Defines Its Narrow Temporal Requirement During Embryonic Hematopoietic Development", Stem Cells, 30, (2012), 1521-1531.
Wu, Hongxia, et al., "Transcriptional regulation of vertebrate heart morphological development", (w/ English Abstract), Life Science Research, vol. 6, No. 4 (Suppl.), (Dec. 2002), 101-105.
U.S. Appl. No. 15/554,585, filed Aug. 30, 2017, ETV2 and Uses Thereof.
U.S. Appl. No. 15/739,042, filed Dec. 21, 2017, Humanized Skeletal Muscle, U.S. Pat. No. 10,874,092.
U.S. Appl. No. 15/739,066, filed Dec. 21, 2017, Humanized Heart Muscle, U.S. Pat. No. 10,897,880.
U.S. Appl. No. 17/118,981, filed Dec. 11, 2020, Humanized Heart Muscle.
"U.S. Appl. No. 15/554,585, 312 Amendment filed Apr. 4, 2023", 3 pgs.
"U.S. Appl. No. 15/554,585, Notice of Allowance mailed Jan. 30, 2023", 9 pgs.
"U.S. Appl. No. 15/554,585, PTO Response to Rule 312 Communication mailed Apr. 17, 2023", 2 pgs.
"U.S. Appl. No. 17/118,981, Response filed Jun. 27, 2023 to Restriction Requirement mailed Mar. 16, 2023", 6 pgs.
"U.S. Appl. No. 17/118,981, Restriction Requirement mailed Mar. 16, 2023", 8 pgs.
"Korean Application Serial No. 10-2017-7027376, Notice of Preliminary Rejection mailed Feb. 27, 2023", w/ English Translation, 9 pgs.
"U.S. Appl. No. 17/118,981, Non Final Office Action mailed Sep. 11, 2023", 23 pgs.
"U.S. Appl. No. 17/118,981, Response filed Mar. 11, 2024 to Non Final Office Action mailed Sep. 11, 2023", 7 pgs.
"U.S. Appl. No. 18/309,466, Preliminary Amendment filed Aug. 4, 2023", 8 pgs.
"European Application Serial No. 16759528.9, Summons to Attend Oral Proceedings mailed Oct. 2, 2023", 3 pgs.
"Korean Application Serial No. 10-2017-7027376, Final Office Action mailed Dec. 5, 2023", w/ English Translation, 7 pgs.
"Korean Application Serial No. 10-2017-7027376, Request for Re-examination filed Mar. 5, 2024 to Final Office Action mailed Dec. 5, 2023", w/ English claims, 7 pgs.
"Korean Application Serial No. 10-2017-7027376, Response filed Jul. 27, 2023 Notice of Preliminary Rejection mailed Feb. 27, 2023", w/ English claims, First page should not be there, but Adobe will not let me delate and I do not know why., 18 pgs.
"Korean Application Serial No. 10-2018-7002387, Notice of Preliminary Rejection mailed Sep. 21, 2023", W/English Translation, 9 pgs.
Hudson, , Stem cells and development 21, (2012), 1513-1523.
"U.S. Appl. No. 17/118,981, Final Office Action mailed Jun. 4, 2024", 9 pgs.
"U.S. Appl. No. 18/309,466, Non Final Office Action mailed Jun. 20, 2024", 22 pgs.

* cited by examiner

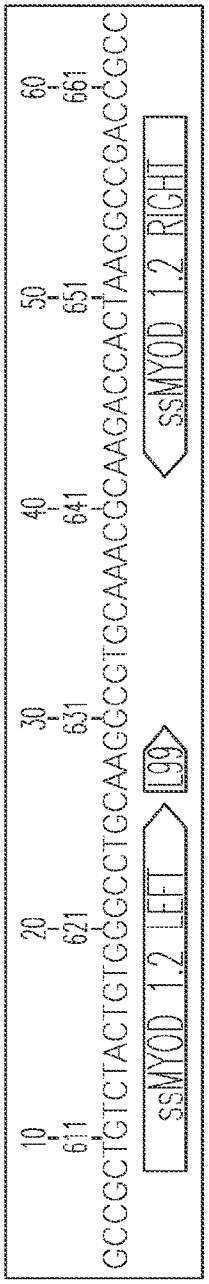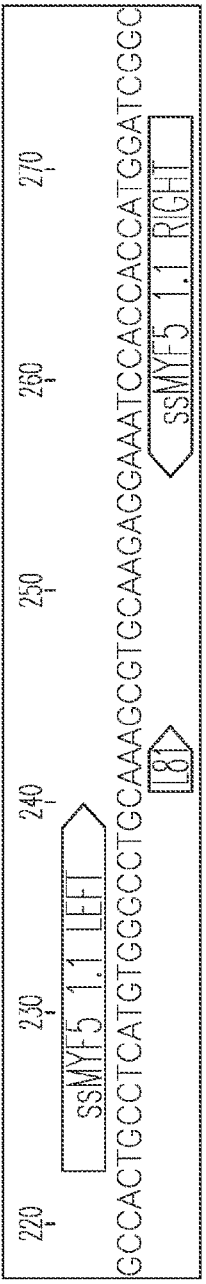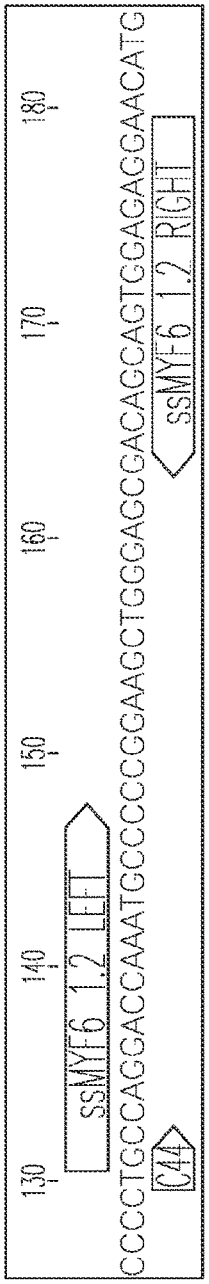
Fig. 3A

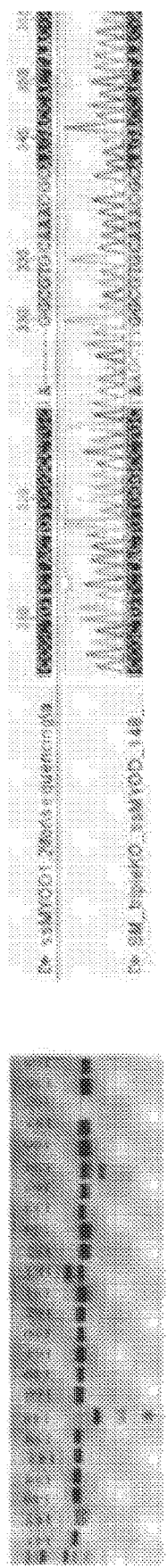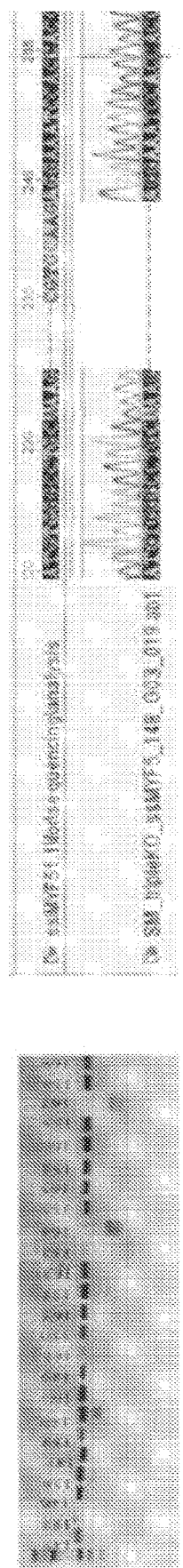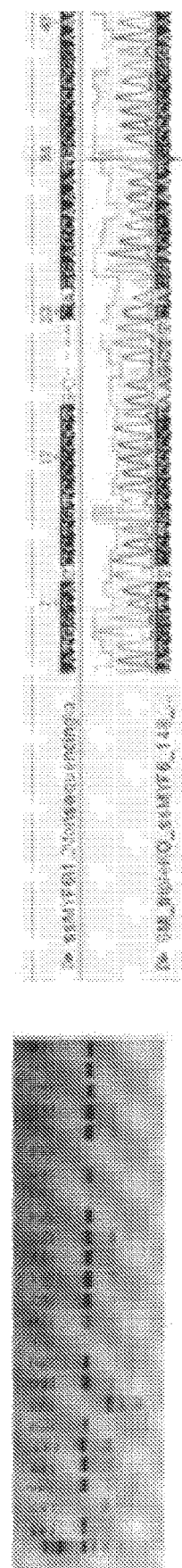
Fig. 3C

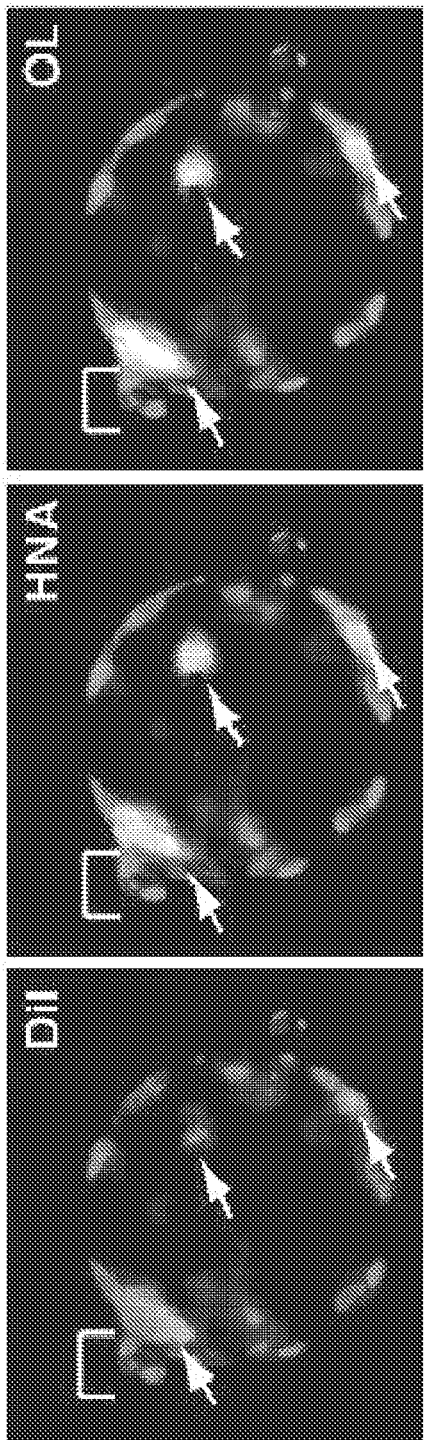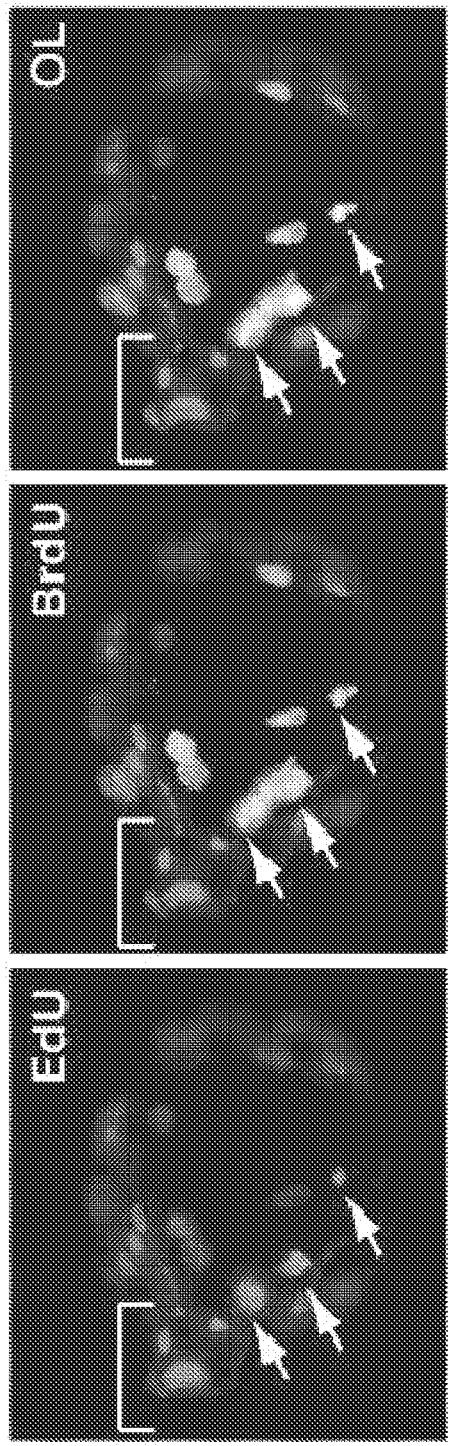

HUMANIZED SKELETAL MUSCLE

CLAIM OF PRIORITY

This application is a divisional of U.S. application Ser. No. 15/739,042, filed Dec. 21, 2017, which is a U.S. National Stage Filing under 35 U.S.C. § 371 of International Application No. PCT/US2016/040378, filed Jun. 30, 2016 and published as WO 2017/004367 on 5 Jan. 2017, which application claims the benefit of priority of U.S. Provisional Patent Application No. 62/187,027, filed 30 Jun. 2015, the benefit of priority of which is claimed hereby, and which is incorporated by reference herein in their entirety.

INCORPORATION BY REFERENCE OF SEQUENCE LISTING

A Sequence Listing is provided herewith as a text file, "2111444.txt" created on Jul. 12, 2023 and having a size of 8,854 bytes. The contents of the text file are incorporated by reference herein in their entirety.

BACKGROUND OF THE INVENTION

Myopathic diseases such as muscular dystrophies are common and deadly. Additionally, many muscular conditions, such as atrophy and sarcopenia are associated with aging. While skeletal muscle has a tremendous capacity for regeneration, this potential ultimately fails with disease and aging. No treatments are currently available for terminal muscle diseases and fifty percent of the falls in the elderly lead to their demise.

SUMMARY OF THE INVENTION

Described herein is the development of MYF5/MYOD/MRF4 knockout pigs or other animals, such as cow or goat, as hosts for production of personalized human/humanized muscle/muscle cells for clinical applications.

MYF5/MYOD/MRF4 null porcine embryos have been generated using gene editing technologies. Performing multiple gene edits for MYF5/MYOD/MRF4 created a permissive niche that is repopulated with muscle using human cells with pluripotent capacity, to yield humanized skeletal muscle (e.g., in a non-human animal).

One embodiment provides a non-human animal cell, morula or blastocyst wherein the genome carries a mutation in both alleles of the MYF5 gene, MYOD gene, MRF4 gene or a combination thereof such that the non-human animal cell, morula or blastocyst lacks functional MYF5 protein, MYOD protein, MRF4 protein or a combination thereof. In one embodiment, the mutation is a deletion of the MYF5 gene, MYOD gene, and/or MRF4 gene. In one embodiment, the non-human animal cell, morula or blastocyst is a porcine, bovine, equine or goat.

One embodiment provides a chimeric non-human animal, morula of blastocyst expressing human MYF5, MYOD, and/or MRF4 and lacking expression of said non-human animal MYF, MYOD, and/or MRF4. In one embodiment, the non-human animal produces humanized skeletal muscle cells and/or tissue. In one embodiment, the non-human animal is a porcine, bovine, equine or goat.

One embodiment provides a chimeric pig expressing exogenous pig MYF5, MYOD, MRF4 or a combination thereof and lacking expression of endogenous pig MYF5, MYOD, MRF4 or a combination thereof (a pig-pig chimera).

One embodiment provides a method for producing a chimeric non-human animal expressing a human MYF5 gene, MYOD gene, MRF4 gene or a combination thereof comprising: a) generating a MYF5, MYOD, MRF4 or a combination thereof null non-human animal cell, wherein both copies of the pig MYF5 gene, MYOD gene, MRF4 gene or a combination thereof carry a mutation that prevents production of functional MYF5 protein, MYOD protein, MRF4 protein or a combination thereof in said non-human animal; b) creating a MYF5, MYOD, MRF4 or a combination thereof null non-human morula or blastocyst by somatic cell nuclear transfer comprising fusing a nucleus from said MYF5, MYOD, MRF4 or a combination thereof null non-human animal cell of a) into an enucleated non-human oocyte and activating said oocyte to divide so as to form a MYF5, MYOD, MRF4 or a combination thereof null non-human morula or blastocyst; c) introducing human stem cells into the MYF5, MYOD, MRF4 or a combination thereof null non-human morula or blastocyst of b); and d) implanting said morula or blastocyst from c) into a pseudopregnant surrogate non-human animal to generate a chimeric non-human animal expressing human MYF5, MYOD, MRF4 or a combination thereof.

Another embodiment provides a method for producing a chimeric pig expressing an exogenous MYF5 gene, MYOD gene, MRF4 gene or a combination thereof comprising a) generating a MYF5, MYOD, MRF4 or a combination thereof null pig cell, wherein both copies of the endogenous pig MYF5 gene, MYOD gene, MRF4 gene or a combination thereof gene carry a mutation that prevents production of functional endogenous pig MYF5 protein, MYOD protein, MRF4 protein or combination thereof; b) creating a MYF5, MYOD, MRF4 (r a combination thereof null pig morula or blastocyst by somatic cell nuclear transfer comprising fusing a nucleus from said MYF5, MYOD, MRF4 or a combination thereof null pig cell of a) into an enucleated pig oocyte and activating said oocyte to divide so as to form a MYF5, MYOD, MRF4 or a combination thereof null pig morula or blastocyst; c) introducing pig stein cells into the pig MYF5, MYOD, MRF4 or a combination thereof null morula or blastocyst of b); and d) implanting said morula or blastocyst from cl into a pseudopregnant surrogate pig to generate a chimeric pig expressing exogenous pig MYF5, MYOD, MRF4 or a combination thereof.

One embodiment provides a method of producing human and/or humanized skeletal muscle cells in a non-human animal comprising: a) generating a MYF5, MYOD, MRF4 or a combination thereof mill non-human animal cell, wherein both alleles of the non-human animal MYF5 gene, MYOD gene, MRF4 gene or a combination thereof carry a mutation that prevents production of functional MYF5 protein, MYOD protein, MRF4 protein or combination thereof; b) creating a MYF5, MYOD, MRF4 or a combination thereof null non-human animal blastocyst or morula by somatic cell nuclear transfer comprising fusing a nucleus from said MYF5, MYOD, MRF4 or a combination thereof null non-human animal cell of a) into an enucleated non-human oocyte and activating said oocyte to divide so as to form a MYF5, MYOD, MRF4 or a combination thereof null non-human morula or blastocyst; c) introducing human donor stem cells into the MYF5, MYOD, MRF4 or a combination thereof null non-human blastocyst or morula of b), and d) implanting said blastocyst or morula from c into a pseudopregnant surrogate non-human animal so as to generate a non-human animal expressing human or humanized skeletal muscles cells.

In one embodiment, the non-human animal is a porcine, bovine, equine or goat. In another embodiment, the human donor stem cell is a tissue specific stem cell, pluripotent stem cell, multipotent adult stem cell, induced pluripotent stem cell or umbilical cord blood stem cell (UCBSC). In one embodiment, the induced pluripotent cell is formed from a fibroblast cell.

One embodiment comprises a non-human animal produced by the methods described herein.

In one embodiment provides a pig cell, morula or blastocyst wherein the genome carries a mutation (such as an early stop codon or deletion) in both alleles of the MYF5 gene, MYOD gene, MRF4 gene or a combination thereof such that the pig cell or blastocyst lacks functional MYF5 protein, MYOD protein, MRF4 protein or a combination thereof. In one embodiment, the mutation is a deletion of the MYF5 gene, MYOD gene, MRF4 gene or a combination thereof.

One embodiment provides a chimeric pig expressing human MYF5, MYOD, MRF4 or a combination thereof and lacking expression of pig MYF5, MYOD, MRF4 or a combination thereof. In one embodiment, the chimeric pig produces humanized skeletal muscle cells and/or tissue.

Another embodiment provides a chimeric pig expressing pig MYF5, MYOD, MRF4 obtained from a pig stem cells (a pig-pig chimera).

One embodiment provides a method for producing a chimeric pig expressing a human MYF5 gene, MYOD gene, MRF4 gene or a combination thereof comprising: at generating a MYF5, MYOD, MRF4 or a combination thereof null pig cell, wherein both copies of the pig MYF5 gene, MYOD gene, MRF4 gene or a combination thereof gene carry a mutation that prevents production of functional pig MYF5 protein, MYOD protein, MRF4 protein or combination thereof; b) creating a MYF5, MYOD, MRF4 or a combination thereof null pig morula or blastocyst by somatic cell nuclear transfer comprising fusing a nucleus from said MYF5, MYOD, MRF4 or a combination thereof null pig cell of a) into an enucleated pig oocyte and activating said oocyte to divide so as to form a MYF5, MYOD, MRF4 or a combination thereof null pig morula or blastocyst c) introducing human stein cells into the pig MYF5, MYOD, MRF4 Or a combination thereof null morula or blastocyst of b); and d) implanting said morula or blastocyst from c) into a pseudopregnant surrogate pig to generate a chimeric pig expressing human MYF5, MYOD, MRF4 (and human skeletal muscle) or a combination thereof.

Another embodiment provides a method of producing humanized skeletal muscle cells in pigs comprising: a) generating a MYF5, MYOD, MRF4 or a combination thereof null pig cell, wherein both alleles of the pig MYF5 gene, MYOD gene, MRF4 gene or a combination thereof carry a mutation that prevents production of functional pig MYF5 protein, MYOD protein, MRF4 protein or combination thereof; b) creating a MYF5, MYOD, MRF4 or a combination thereof null pig morula or blastocyst by somatic cell nuclear transfer comprising fusing a nucleus from said MYF5, MYOD, MRF4 or a combination thereof null pig cell of a) into an enucleated pig oocyte and activating said oocyte to divide so as to form a MYF5, MYOD, MRF4 or a combination thereof null pig morula or blastocyst; c) introducing human stem cells into the pig MYF5, MYOD, MRF4 or a combination thereof null morula or blastocyst of b); and d) implanting said morula or blastocyst from c) into a pseudopregnant surrogate pig so as to generate a pig expressing humanized skeletal muscles cells.

In one embodiment, the methods use a human induced pluripotent stem cell or a human umbilical cord blood stem cell. In one embodiment, the methods use a human induced pluripotent cell is formed from a fibroblast cell.

One embodiment provides a gene knockout pig cell or blastocyst wherein the genome comprises a deletion of the MYF5, MYOD, MRF4 gene(s) or a combination thereof gene such that the pig cell or blastocyst lacks functional MYF5, MYOD, MRF4 protein or a combination thereof, wherein the pig cell or blastocyst is homozygous for the deletion. In one embodiment, the sequence of wild type pig (Sus scrofa) MYF5 is provided at MYF5 ENSSSCG00000937 (MYF5 ENSG00000111049), MYOD is provided at MYOD NC_010444 (Human Gene: MYOD ENSG00000124152), and MRF4 (also known as MYF6) is provided at MYF6 ENSSSCG0000026533 (Human Gene: MYF6 ENSG00000111046).

It would be useful to make human or humanized tissues and organs personalized to each recipient's immune complex. As disclosed herein, it is possible to do so by using a large animal as a host and editing its genome to knock out or debilitate genes responsible for the growth and/or differentiation of a target organ and inoculating that animal at a blastocyst or zygote stage with donor stem cells to complement the missing genetic information for the growth and development of the organ. The result is a chimeric animal in which the complemented tissue (human/humanized organ) matches the genotype and phenotype of the donor. Such organs may be made in a single generation and the stem cell may be taken or generated from the patient's own body. As disclosed herein, it is possible to do so by simultaneously editing multiple genes in a cell (see, for example, WO 20151/168125, which is incorporated herein by reference). Multiple genes can be targeted for editing using targeted nucleases and homology directed repair (HDR) templates in vertebrate cells or embryos.

BRIEF DESCRIPTION OF THE DRAWINGS

FIGS. 3A-C (A.) TALEN pairs were designed for swine MYOD, MYF5, and MYF6 (aka MRF4) genes. TALEN binding sites (denoted by arrow heads) were upstream of the basic (+) helix-loop-helix (HLH) domain for each gene. The TALEN binding sites are shown above (denoted by arrows) and the amino acid that was targeted for a premature STOP codon by homology dependent repair (HDR) are denoted by arrows (SEQ ID NOs: 22-24). (B.) 1500 ng of each TALEN pair was simultaneously transfected into primary swine fibroblasts along with 0.1 nmol of each of the 90mer HDR oligos designed to introduce the premature STOP codon and a novel restriction enzyme recognition site (HindIII) to allow facile analysis of HDR events. The region of interest for each gene was amplified by PCR and restriction fragment length polymorphism (RFLP) was assessed for the population of transfected cells. The closed arrow heads denote the uncut or wild type alleles, while the open arrow heads denote the HDR alleles. The percent of alleles positive for HDR for MYOD, MYF5, and MYF6 were 14%, 31%, and 36%, respectively. (C.) These populations were plated out for individual colony isolation. 38 out of 768 (4.9%) colonies demonstrated 4 or more RFLP events and were further analyzed by sequencing. Five clones were identified to be homozygous knockout for all three genes by either HDR incorporating the premature STOP codon or indels that would result in a frameshift and subsequent premature STOP codon. An example of the RFLP analysis and sequencing of a clone that is a triple knockout for MYOD/MYF5/MYF6 is shown.

FIGS. 5A-B depict (A) Blastocyst with DiI-labeled hiPSC in the ICM. Arrows indicate cells positive for DiI and HNA. (B) Blastocyst with EdU-labeled hiPSCs in the ICM. hiPSC were labeled with 40 µM EdU for 24 hours and injected. Blastocysts were pulsed with 10 µM BrdU for an hour to label dividing cells. Double positive cells are indicated by arrows. BrdU+/EdU− cells are dividing host cells. Note that the blastocysts are beginning to hatch (brackets), which signifies developmental progression.

DETAILED DESCRIPTION OF THE INVENTION

Figure 1:
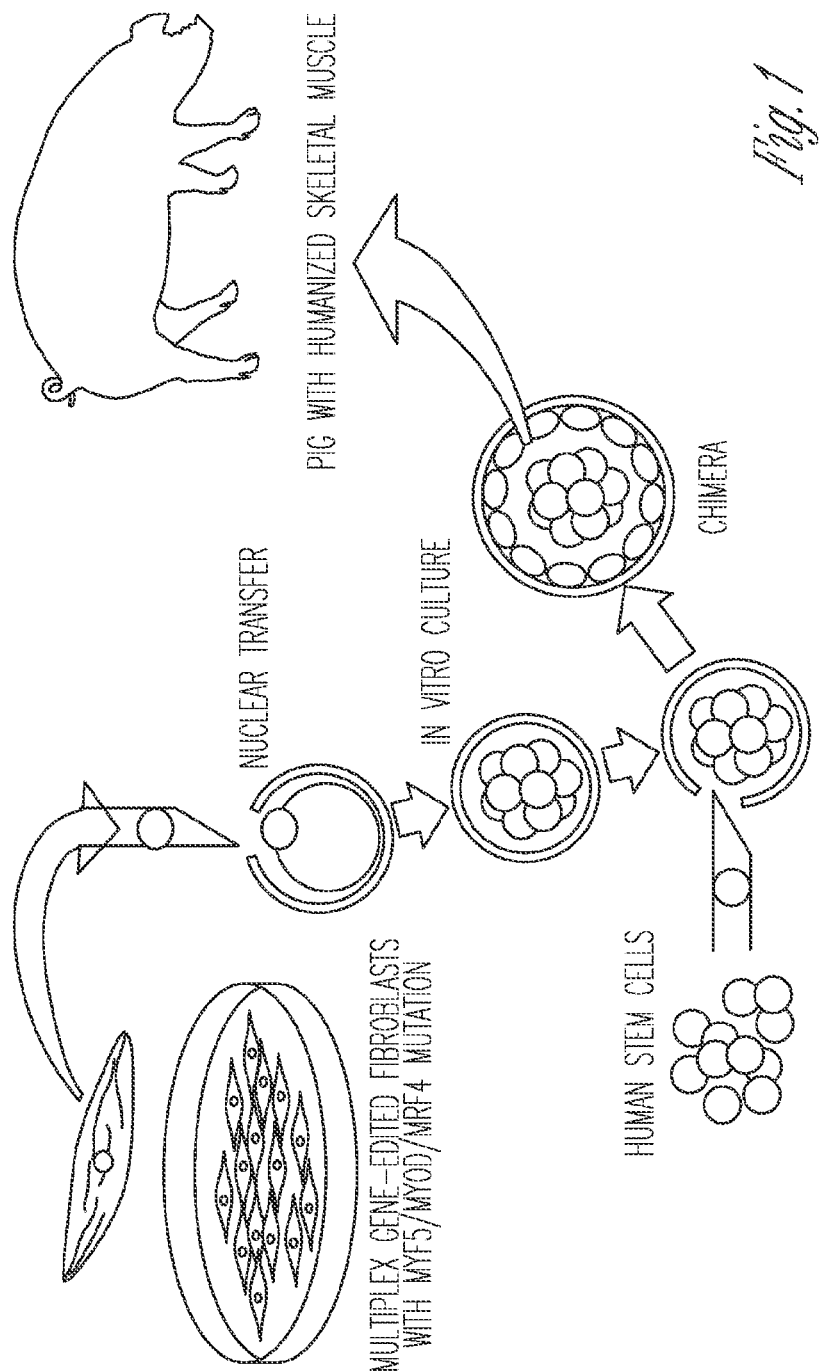
FIG. 1 depicts the overall strategy to produce humanized skeletal muscle in a pig model. Multiplex gene editing is utilized to produce MYF5/MYOD/MRF4 mutant pig fibroblasts, SCNT and human stem cell delivery to engineer a pig with humanized skeletal muscle.
Figures 2A, 2B:
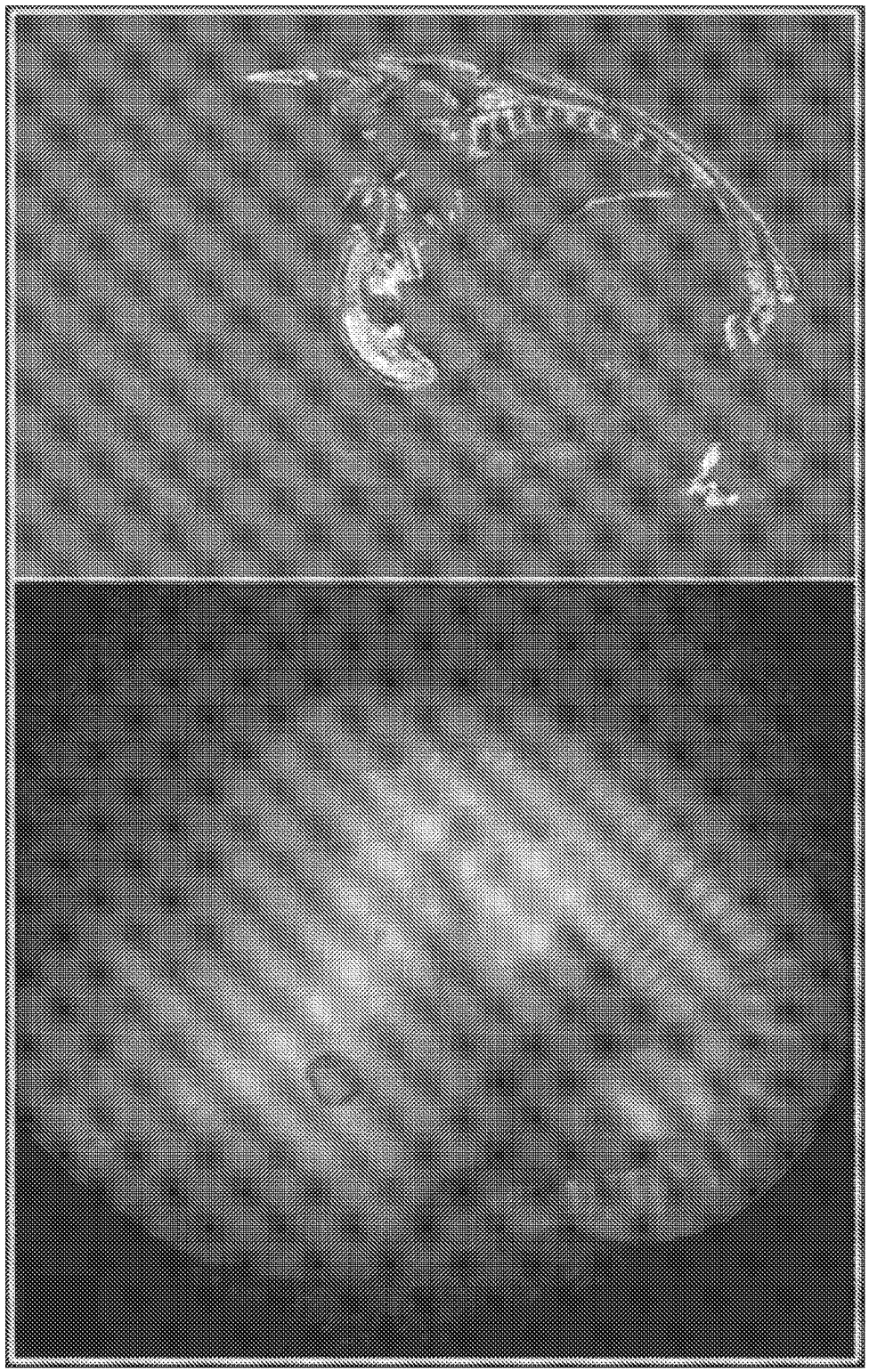
FIGS. 2A-B demonstrate that Myf5, Myod and Mrf4 are muster regulators of skeletal muscle and are restricted to skeletal muscle in development and in the adult. Shown here is Myod-GFP transgenic expression which is restricted to the somites, diaphragm and established skeletal muscle in mouse at E11.5 (panel A). In panel B, in situ hybridization of a parasagittal section of a E13.5 (mid-gestation) mouse embryo using a 35S-labeled MyoD riboprobe. Note expression in back, intercostal and limb muscle groups (9).

MYF5/MYOD/MRF4 null porcine embryos have been generated using gene editing technologies. Performing multiple gene edits for MYF5/MYOD/MRF4 creates a permissive niche that is repopulated with muscle using pig cells with pluripotent capacity, and will be repopulated with human stem cells to yield humanized skeletal muscle in a non-human animal.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as Hawley's Condensed Chemical Dictionary 14th Edition, by R. J. Lewis, John Wiley & Sons, New York, N.Y., 2001.

References in the specification to "one embodiment," "an embodiment," etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

As used herein, the articles "a" and "an" refer to one or to more than one, i.e., to at least one, of the grammatical object of the article. By way of example, "an element" means one element or more than one element.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

As used herein, "or" should be understood to have the same meaning as "and/or" as defined above. For example, when separating a listing of items, "and/or" or "or" shall be interpreted as being inclusive, e.g., the inclusion of at least one, but also including more than one, of a number of ems, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other bit not both") when preceded by terms of exclusivity, such as "either," "one of," "only one of," or "exactly one of."

As used herein, the terms "including," "includes," "having," "has," "with," or variants thereof, are intended to be inclusive similar to the term "comprising."

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to," "at least," "greater than," "less than," "more than," "or more," and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group.

Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "isolated" refers to a factor(s), cell or cells which are not associated with one or more factors, cells or one or more cellular components that are associated with the factor(s), cell or cells in vivo.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The terms "cell," "cell line," and "cell culture" as used herein may be used interchangeably. All of these terms also include their progeny, which are any and all subsequent generations. It is understood that all progeny may not be identical due to deliberate or inadvertent mutations.

"Cells" include cells from, or the "subject" is, a vertebrate, such as a mammal, including a human. Mammals include, but are not limited to, humans, farm animals, sport animals and companion animals. Included in the term "animal" is dog, cat, fish, gerbil, guinea pig, hamster, horse, rabbit, swine, mouse, monkey (e.g., ape, gorilla, chimpanzee, or orangutan), rat, sheep, goat, cow and bird.

In one embodiment, the stem, progenitor or precursor cells are embryonic stem cells, adult stem cells, induced pluripotent stem cells, and/or multipotent stem cells (such as multipotent mesodermal precursors). In one embodiment, the stem, progenitor or precursor cells are mammalian cells. In one embodiment, the stein cells include, but are not limited to, induced pluripotent stem cells, umbilical blood cord stem cells, mesenchymal stem cells, pluripotent stem cells. In one embodiment, the stem cells are of human origin. In another embodiment, the stem cells are of pig origin.

Totipotent (a.k.a. omnipotent) stem cells can differentiate into embryonic and extraembryonic cell types. Such cells can construct a complete, viable organism. These cells are produced from the fusion of an egg and sperm cell. Cells produced by the first few divisions of the fertilized egg are also totipotent. Pluripotent stem cells are the descendants of totipotent cells and can differentiate into nearly all cells, i.e. cells derived from any of the three germ layers. Multipotent stem cells can differentiate into a number of cell types, but only those of a closely related family of cells. Oligopotent stem cells can differentiate into only a few cell types, such as lymphoid or myeloid stein cells. Unipotent cells can produce only one cell type, their own, [4] but have the property of self-renewal, which distinguishes them from non-stem cells (e.g. progenitor cells, muscle stem cells).

"Expansion" refers to the propagation of cells without differentiation.

"Progenitor cells" are cells produced during differentiation of a stem cell that have some, but not all, of the characteristics of their terminally-differentiated progeny. Defined progenitor cells are committed to a lineage, but not to a specific or terminally-differentiated cell type. The phrase "endothelial cells" encompasses not only terminally-differentiated cells types, but also cells that are committed to an endothelial lineage, but are not terminally-differentiated.

"Differentiation factors" refer to cellular factors, preferably growth factors or angiogenic factors that induce lineage commitment.

The terms "pig," "swine" and "porcine" are used interchangeably and are generic terms referring to the same type of animal without regards to gender, size or breed. It is also noted that terms "pig," "swine" and "porcine", such as the null "pig," "swine" and "porcine" that is complemented with human or pig genes, the "pig," "swine" and "porcine" may be embryos, neonates or adults (including newborns and young pigs).

As used herein, the phrase "humanized skeletal muscle" refers to cells or tissue in a pig or other non-human animal that express one more human genes and/or proteins. In one embodiment, the pig cells or tissue that express one more human genes/proteins do not express the corresponding functional pig gene and/or protein.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when adminstered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, a "functional" biological molecule is a biological molecule in a form in which it exhibits a property by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit positon in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator using the BLAST tool at the NCBI website. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0. BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NB LAST) can be used.

The percent identity between two sequences can be determined using techniques similar to those described above, with or without allowing gaps. In calculating percent identity, typically exact matches are counted.

As used herein, an "instructional material" includes a publication, a recording, a diagram, or any other medium of expression which can be used to communicate the usefulness of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified invention, or portion thereof, or be shipped together with a container which contains the invention or portion thereof. Alternatively, the instructional material may be shipped separately from the container with the intention that the instructional material and the compound be used cooperatively by the recipient.

As used herein, the term "nucleic acid" encompasses RNA as well as single and double stranded DNA and cDNA. Furthermore, the terms, "nucleic acid," "DNA," "RNA" and similar terms also include nucleic acid analogs, i.e. analogs having other than a phosphodiester backbone. For example, the so called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorthioate, methylphosphonate, phosphorodithioate, bridged phosphorothioate or sulfone linkages, and combinations of such linkages. The term nucleic acid also specifically includes nucleic acids composed of bases other than the live biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U"replaces"."

Transcription Activator-Like Effector Nucleases (TALENs) are artificial restriction enzymes generated by fusing the TAL effector DNA binding domain to a DNA cleavage domain. These reagents enable efficient, programmable, and specific DNA cleavage for genome editing in situ. Transcription activator-like effectors (TALEs) are proteins that bind DNA in a sequence specific way. By fusing such a TALE to a nuclease (e.g., FokI endonuclease) a highly specific DNA "scissor" is made (these molecules can be engineered to bind any DNA sequence). The term TALEN, as used herein, is broad and includes a monomeric TALEN that can cleave double stranded DNA without assistance from another TALEN. The term TALEN is also used to refer to one or both members of a pair of TALENs that are engineered to work together to cleave DNA at the same site. TALENs that work together may be referred to as a left-TALEN and a right-TALEN, which references the handedness of DNA.

Once the TALEN genes have been assembled they are inserted into plasmids; the plasmids are then used to transfect the target cell where the gene products are expressed and enter the nucleus to access the genome. TALENs can be used to edit genomes by inducing double-strand breaks (DSB) and optionally inserting a cargo/preselected gene, which cells respond to with repair mechanisms. In this manner, they can be used to correct mutations in the genome which, for example, cause disease.

Genetic engineering, including gene editing, can be carried out by any method available to an art worker, for example, by the use of targeted endonucleases, and homology directed repair (HDR), TALEN, CRISPR (e.g., CAS9/CRISPR), recombinase fusion molecules, synthetic porcine artificial chromosomes, meganucleases, zinc linger or rAAV based systems for gene editing (e.g., to knockout desired target genes). Further, a variety of nucleic acids can be introduced into cells, for knockout purposes, for inactivation of a gene (such as interfering RNAs (shRNA, siRNA, dsRNA, RISC, miRNA) or express a gene.

Somatic cell nuclear transfer (SCNT) is a laboratory technique for creating a viable embryo from a body cell and an egg cell. The process of somatic cell nuclear transplant involves two different cells. The first being a female gamete, known as the ovum (egg/oocyte). The second being a somatic cell, referring to the cells of the human body. Skin cells, fat cells, and liver cells are only a few examples. The nucleus of the donor egg cell is removed and discarded, leaving it 'deprogrammed.' The nucleus of the somatic cell is also removed but is kept, the enucleated somatic cell is discarded. What is left is a lone somatic nucleus and an enucleated egg cell. These are then fused by squirting the somatic nucleus into the 'empty' ovum. After being inserted into the egg, the somatic cell nucleus is reprogrammed by its host egg cell. The ovum, now containing the somatic cell's nucleus, is stimulated with a shock and will begin to divide. The egg is now viable and capable of producing an adult organism containing all the necessary genetic information from just one parent. Development will ensue normally and after many mitotic divisions, this single cell forms a blastocyst (an early stage embryo with about 100 cells) with an identical genome to the original organism (i.e. a clone). Stem cells can then be obtained by the destruction of this clone embryo for use in therapeutic cloning or in the case of reproductive cloning the clone embryo is implanted into a host mother (pseudopragnant/surrogate) for further development and brought to term.

"Chimera" refers to is a single organism composed of genetically distinct cells.

"Humanized" refers to an organ or tissue harvested from a non-human animal whose protein sequences and genetic complement are more similar to those of a human than the non-human host.

"Organ" refers to a collection of tissues joined in a structural unit to serve a common function. "Tissue" as used herein refers to a collection of similar cells from the same origin that together carry out a specific function.

A nullizygous organism carries two mutant or missing alleles for the same gene. The mutant/missing alleles are both complete loss-of-function or 'null' alleles, so homozygous null and nullizygous are synonymous.

A gene knockout (abbreviation: KO) is a genetic technique in which both of an organism's alleles are made inoperative ("knocked out" of the organism). The term knockout, inactivated, and disrupted are used interchangeably herein to mean that the targeted site is changed so that the gene expression product is eliminated or greatly reduced. Also known as knockout organisms or simply knockouts. The term also refers to the process of creating such an organism as in "knocking out" a gene. The technique is essentially the opposite of a gene knockin.

The term gene is broad and refers to chromosomal DNA that is expressed to make a functional product Genes have alleles. Gene editing may be mon-allelic or bi-allelic.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant cell" is a cell that comprises a transgene. Such a cell may be a eukaryotic or a prokaryotic cell. Also, the transgenic cell encompasses, but is not limited to, an embryonic stem cell comprising the transgene, a cell obtained from a chimeric mammal derived from a transgenic embryonic stem cell where the cell comprises the transgene, a cell obtained from a transgenic mammal, or fetal or placental tissue thereof, and a prokaryotic cell comprising the transgene.

The term "regulate" refer to either stimulating or inhibiting a function or activity of interest.

As used herein, a "subject in need thereof" is a patient, animal, mammal, or human, who will benefit from the invention.

As used herein, a "substantially homologous amino acid sequences" includes those amino acid sequences which have at least about 95c homology, preferably at least about 96% homology, more preferably at least about 97% homology, even more preferably at least about 98% homology, and most preferably at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. Preferably, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 99% or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M NaPO4, 1 mM EDTA at 50° C. with washing in 2× standard saline citrate (SSC), 0.1% SDS at 50° C.; preferably in 7% (SDS), 0.5 M NaPO4, 1 mM EDTA at 50° C. with washing in 1×SSC, 0.1% SDS at 50° C.; preferably 7% SDS, 0.5 M NaPO4, 1 mM EDTA at 50° C. with washing in 0.5×SSC, 0.1% SDS at 50° C.; and more preferably in 7% SDS, 0.5 M NaPO4, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984 Nucl. Acids Res. 12:387), and the BLASTN or FASTA programs (Altschul et al., 1990 Proc. Natl. Acad. Sci. USA. 1990 87:14:5509-13; Altschul et al., J. Mol. Biol. 1990 215:3:403-10; Altschul et al., 1997 Nucleic Acids Res. 25:3389-3402). The default settings provided with these programs are suitable for determining substantial similarity of nucleic acid sequences for purposes of the present invention.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

Methods involving conventional molecular biology techniques are described herein. Such techniques are generally known in the art and are described in detail in methodology treatises, such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts, 22: 1859-1862, 1981, and Matteucci et al., J. Am. Chem. Soc. 103:3185, 1981.

The term "comprises" "comprising," and the like can have the meaning ascribed to them in U.S. Patent Law and can mean "includes," "including" and the like. As used herein, "including" or "includes" or the like means including, without limitation.

Exogenic Organ/Tissue Production

The humanized large animal model is a resource for regenerative medicine and will serve as a platform for personalized humanized porcine models. This strategy will transform the current clinical practice paradigms for chronic musculoskeletal diseases and transplantation. Ablation of porcine skeletal muscle is unique, because it not only aims to develop humanized skeletal muscle in a large animal model, but because it is a novel approach to circumvent immune rejection, and can be broadly applicable for exogenic organ development strategies.

Currently, limited therapies are available for progressive muscle weakness, musculoskeletal diseases (such as genetic disease such as muscular dystrophy) or sarcopenia (muscle weakness and wasting associated with the aging process). In some cases, the only definitive therapy for advanced end-stage organ failure or needed tissue to treat a condition/disease is transplantation. The limiting factor for transplantation is donor organ/tissue availability. Hundreds of thousands of patients could benefit from such therapy, but are not suitable transplant candidates due to their comorbid diseases. Therefore, there is a significant shortage of cadaveric or living-related donor organs/tissue. Furthermore, transplantation of organs or tissue requires lifelong immunosuppression which also has deleterious side effects. Herein the generation of humanized tissues, in particular muscle tissue, in pigs is described, which will serve as an unlimited source of whole muscle for transplantation and provide a paradigm shifting platform for treatment of a number of disease and/or conditions diseases.

Interest has focused on xenogeneic transplantation. For example, a rat pancreas was produced in a mouse by the process of blastocyst complementation (27). In these studies, blastocysts mutant for Pdx1, the master regulatory gene for pancreatic development, were injected with pluripotent stem cells from wild-type (Wt) rat (rPSCs) (27). Transfer of the rPSC-injected blastocysts into surrogate mouse dams give rise to mouse chimeras with functional pancreata composed of rat cells. These studies demonstrate the generation of blastocysts deficient in a key developmental regulatory factor, so that the embryo completely lacks the target organ/tissue. These mutant hosts then provide a developmental "niche," for the healthy donor stem cells to populate and generate a donor-derived organ and/or tissue. The blastocyst complementation strategy has also produced organs such as the kidney, thymus and liver in rodents, and recently the pancreas in pigs (28-31).

Using a gene-editing platform, various developmental genes can be mutated to generate organ and/or tissue deficient pigs, upon which blastocyst complementation can be deployed for the generation of exogenic organs and/or tissue. The efficiency of this system allows many genes to be tested empirically. The simultaneous modification of multiple regulatory genes permits the modulation of complex tissue ontogeny.

Muscle Diseases/Disorders

Muscles help you move and help your body work. Different types of muscles have different jobs. There are many problems that can affect muscles. Muscle disorders can cause weakness, pain or even paralysis.

Causes of muscle diseases/disorders include injury or overuse, such as sprains or strains, cramps or tendinitis; a genetic disorder, such as muscular dystrophy, cancer, inflammation, such as myositis, diseases of nerves that affect muscles, infections and certain medicines.

Myopathy is a muscular disease in which the muscle fibers do not function for any one of many reasons, resulting m muscular weakness. "Myopathy" simply means muscle disease (myo-Greek μυο "muscle"+pathos-pathy Greek "suffering"). This meaning implies that the primary defect is within the muscle, as opposed to the nerves ("neuropathies" or "neurogenic" disorders) or elsewhere (e.g., the brain etc.). Muscle cramps, stiffness, and spasm can also be associated with myopathy.

Muscular disease can be classified as neuromuscular or musculoskeletal in nature. Some conditions, such as myositis, can be considered both neuromuscular and musculoskeletal.

Myopathies (also known as muscular dystrophy) in systemic disease results from several different disease processes including hereditary (presenting birth), endocrine, inflammatory (inflammatory myopathies caused by, for example, dermatomyositis, polymyositis; inclusion body myositis, viral (HIV), paraneoplastic, infectious, drug- and toxin-induced (e.g., alcohol, cortosteroids, narcotics, colchicines, chloroquine), critical illness myopathy, metabolic, paraneoplastic myopathy, collagen related, and myopathies with other systemic disorders. Patients with systemic myopathies often present acutely or sub acutely. On the other hand, familial myopathies or dystrophies generally present in a chronic fashion with exceptions of metabolic myopathies where symptoms on occasion can be precipitated acutely. Most of the inflammatory myopathies can have a chance association with malignant lesions; the incidence appears to be specifically increased in patients with dermatomyositis.

There are many types of myopathy:

Inherited forms include: dystrophies ((or muscular dystrophies) are a subgroup of myopathies characterized by muscle degeneration and regeneration. Clinically, muscular dystrophies are typically progressive, because the muscles' ability to regenerate is eventually lost, leading to progressive weakness, often leading to use of a wheelchair, and eventually death, usually related to respiratory weakness), Myotonia, Neuromyotonia, congenital myopathies (which do not show evidence for either a progressive dystrophic process (i.e., muscle death) or inflammation, but instead characteristic microscopic changes are seen in association with reduced contractile ability of the muscles. Congenital myopathies include, but are not limited to: nemaline myopathy (characterized by presence of "nemaline rods" in the muscle), multi/minicore myopathy (characterized by multiple small "cores" or areas of disruption in the muscle fibers), centronuclear myopathy (or myotubular myopathy) (in which the nuclei are abnormally found in the center of the muscle fibers), a rare muscle wasting disorder), mitochondrial myopathies (which are due to defects in mitochondria, which provide a source of energy for muscle), familial periodic paralysis, inflammatory myopathies (which are caused by problems with the immune system attacking components of the muscle, leading to signs of inflammation in the muscle), metabolic myopathies (which result from defects in biochemical metabolism that primarily affect muscle), glycogen storage diseases (which may affect muscle) and/or lipid storage disorder.

Acquired forms include: External substance induced myopathy. Drug-induced myopathy. Glucocorticoid myopathy (is caused by this class of steroids increasing the breakdown of the muscle proteins leading to muscle atrophy), Alcoholic myopathy, Myopathy due to other toxic agents, dermatomyositis produces muscle weakness and skin changes; polymyositis produces muscle weakness, inclusion body myositis (is a slowly progressive disease that produces weakness of hand grip and straightening of the knees), Myositis ossificans, Rhabdomyolysis and/or myoglohinurias.

MYF5/MYOD/NRF4

MYF5/MYOD/MRF4 were mutated to generate skeletal muscle lineage deficient pig embryos (MYF5/MYOD/MRF4 null porcine embryos; see example 2 for details). Specifically, embryos harvested at E18 and E24 were absent of desmin in the myotomes, but cardiac desmin was preserved. Moreover, by injecting GFP labeled porcine blastomeres into null blastocysts, pig:pig complementation was demonstrated using PCR, histological and immuhistological approaches. In these complemented embryos, GFP was colocalized together with desmin in the somites (E24). Performing multiplex gene edits for MYF5/MYOD/MRF4 created a permissive niche that is repopulated with muscle using pig stem cells with pluripotent capacity, to yield wildtype pig skeletal muscle. This gene edited pig model, that lacks MYF5/MYOD/MRF4, will be used to generate humanized skeletal muscle following the delivery of human stem cells into the mutant morula or blastocyst.

The humanized large animal model will be an important resource for regenerative medicine and will serve as a platform for making personalized organs. This strategy can transform the current clinical practice paradigms for muscle diseases and transplantation. To date, exogenic transplantation of organs has been performed between mouse and rat 127, 29); and pig and pig (31), and no successful development of humanized organs in large animal models have been reported. Incorporated herein by reference is U.S. Provisional Application Ser. No. 62/247,092; 62/247,096; and 62/247,122.

The following examples are intended to further illustrate certain embodiments of the invention and are not intended to limit the scope of the invention in any way.

EXAMPLE

Example 1

Materials and Methods

Sow/gilts: Domestic maternal female pigs (8-12 months old) will be used as embryo transfer recipients and cared for and maintained as regular domestic pigs in prospective gestation and farrowing under approved IACUC protocols.

Estrus Synchronization and Insemination: Sows will be given 6.8 mL of Matrix (altrenogest 2.2 mg/mL) mixed into their morning feed on days 11-22 of their estrus cycle to synchronize estrus. Lutalyse (2 cc) will be administered IM on the last day of Matrix and four days later. Sows will be checked for estrus twice daily, starting day 6 alter the end of Matrix administration. The sows will be inseminated with semen from selected boars up to three times alter first detected in estrus. Sows will be checked for pregnancy between days 23-90 of gestation using either Doppler ultrasound or transabdominal ultrasound with a linear 5 mHz transducer. Neither form of ultrasound is invasive and does not harm the sow or fetuses. Blood samples may be taken from the pregnant gilts/sows to determine if any diseases are present at the request of the veterinarian or for genetic analysis.

Embryo Transfer: Reconstructed cloned embryos are surgically transferred into uteri of asynchronous recipient female pigs. For surgical embryo transfer, anesthesia is induced with a combination of the following ketamine (2 mg/kg), tiletamine/zolazepam (0.25 mg/kg), xylazine 1 mg/kg), and atropine (0.03 mg/kg, all from Iowa Veterinary Supply) General anesthesia will be maintained for the rest of the procedure with isoflurane or sevoflurane 45% induction, maintenance at 1-4% to keep at surgical plane). While in dorsal recumbence, the recipients are aseptically prepared for surgery and a caudal ventral incision is made to expose and examine the reproductive tract, including the uterus, oviducts and ovaries. Typically, 150-200 reconstructed cloned embryos are placed in the isthmus of the oviduct using a 5.5-inch TomCat® catheter (Iowa Veterinary Supply). The uterus is placed back into the peritoneal cavity, and the recipient animals are sutured and placed into postoperative recovery. During gestation, real-time ultrasound examination is used to confirm and monitor pregnancy using an Aloka 500 Ultrasound Scanner (Aloka Co. Ltd. Wallingford, CT) with an attached 3.5 MHz trans-abdominal probe. Recipient husbandry will be maintained as normal gestating sows. For piglet production, recipients will be allowed to farrow naturally or will be delivered by c-section prior to day 118 of gestation. Colostrum feeding and intensive neonatal support, including Nurtinger rearing units, are available when necessary.

Myf5, Myod, and Mrf4 are Regulators of Myogenesis

The discovery of the Myod family, including Myod, Myf5 Mrf4, and Myog, provides the fundamental platform for understanding the regulatory mechanisms of skeletal muscle myogenesis (6-8).

Multiple strategies have been employed to investigate the regulatory network of the Myod family during myogenesis, such as transcriptome analysis, promoter analysis and ChIP-seq (6-7; 10), Myod family members are master myogenic regulators as they transactivate a broad spectrum of gene families, including muscle specific genes, transcription factors, cell cycle genes, etc. to promote a myogenic cell fate (6-7; 10-11). Previous gene disruption studies have demonstrated that mice lacking Myf5/Myod/MRF4 lack skeletal muscle and are lethal early following birth presumably due to their inability for respiration (due to the absence of a diaphragm) (8).

Utilizing TALENs and Homology-Dependent Repair (HDR) to Knockout MYOD, MYF5, and MRF4

Figure 3B:
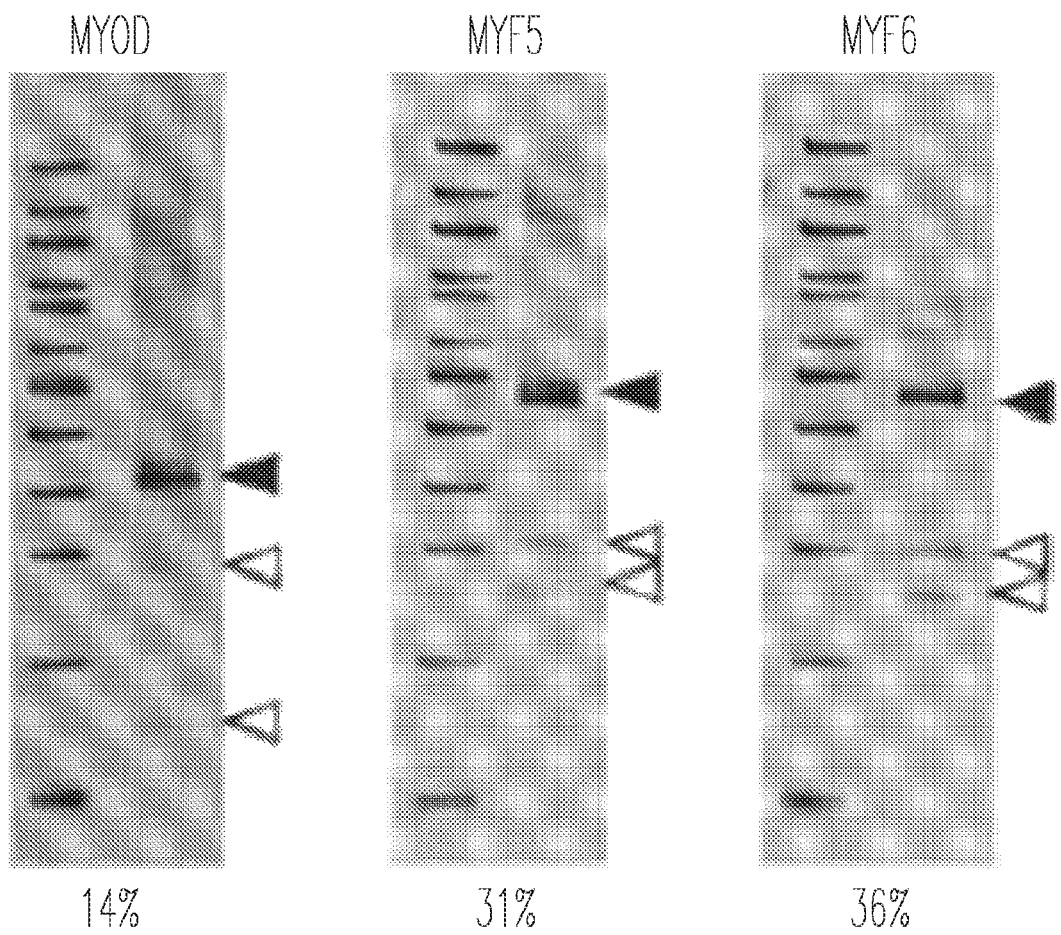

To examine the role of MYF5/MYOD/MRF4 (aka MYF6) in the pig, each coding sequence was removed using two TALEN pairs flanking the gene in porcine fibroblasts (FIG. 3).

MYF5/MYOD/MRF4 Knockout Pig Embryos Lack Skeletal Muscle Lineages

Figure 4A:
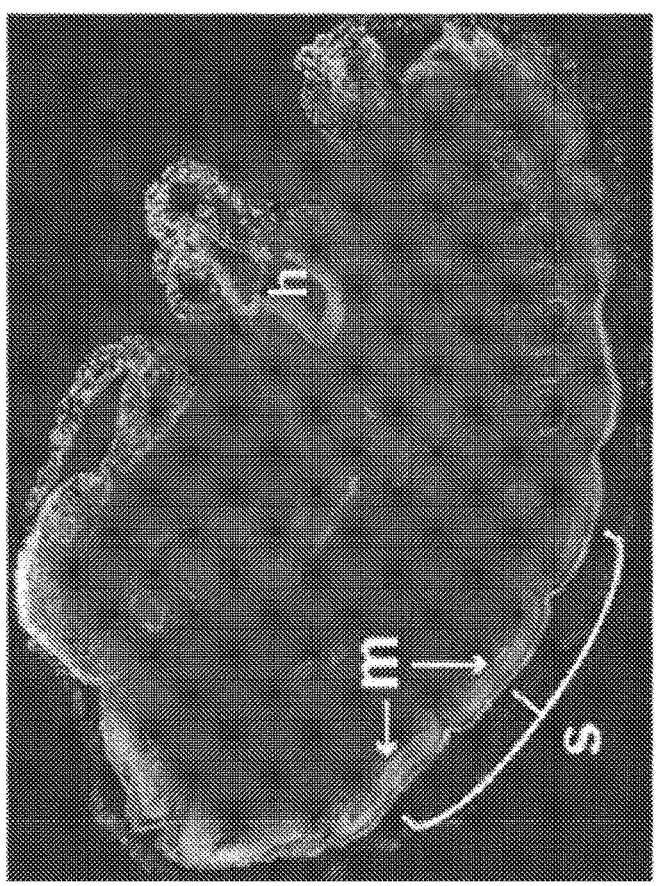
FIGS. 4A-B depict at E18.0, wild-type (Wt) embryos had well defined somites(s), desmin positive myotomes (m) and developing musculature (FIG. 3A). In addition, the developing heart tube demonstrated strong desmin signal (h). In contrast, MYF5/MYOD/MRF4 KO embryos showed a lack of myotome formation while the heart remained desmin positive (FIG. 3B).
Figure 4B:
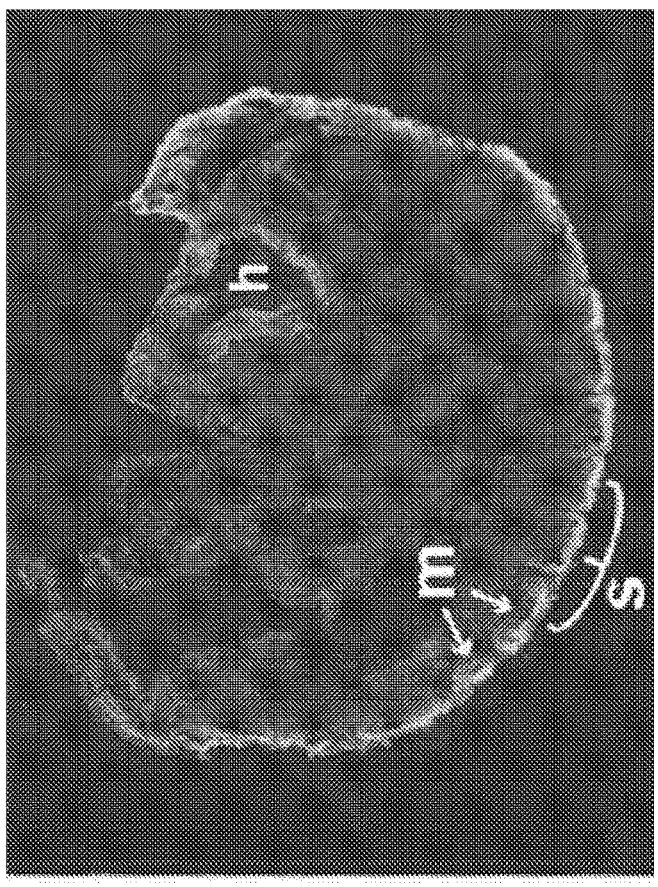
Figure 6A:
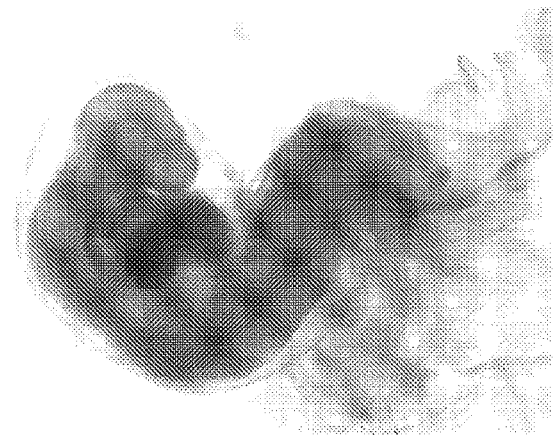
FIGS. 6A-D depict E20 porcine MYF5/MYOD/MRF4 null embryos complemented with GFP labeled blastomeres. Native GFP is observed in whole mount embryos in the liver and yolk sac of the embryo. B. Section of porcine liver from MYF5/MYOD/MRF4 null embryos (E20) complemented with GFP labeled blastomeres. Native GFP is visible in the liver. C. PCR of yolk sac from E20 porcine MYF5/MYOD/MRF4 null embryos complemented with GFP labeled blastomeres (Embryos 1 (shown in panels A, B, D), 3, 5). GFP-labeled pig fibroblasts are a positive control while WT pig liver is a negative control. Titration is performed with GP-labeled fibroblasts. These data indicate that GFP is expressed in approximately 1:10 cells in the yolk sac. D. Section of somite from E20 porcine MYF5/MYOD/MRF4 null embryos complemented with GFP labeled blastomeres demonstrates GFP complementation in present in the somites and that desmin (red) is present in GFP labeled cells (arrowheads). These data demonstrate the ability to successfully perform pig:pig complementation and, further, show that desmin is produced in complemented cells. These data demonstrate the ability of creating a triple knockout in the porcine model devoid of skeletal muscle that will create a niche for the formation of complemented tissues. This approach is used to create humanized skeletal muscle in the pig.
Figure 6B:
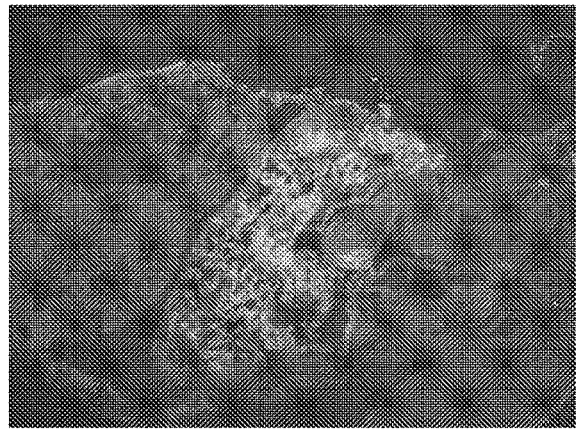
Figure 6C:
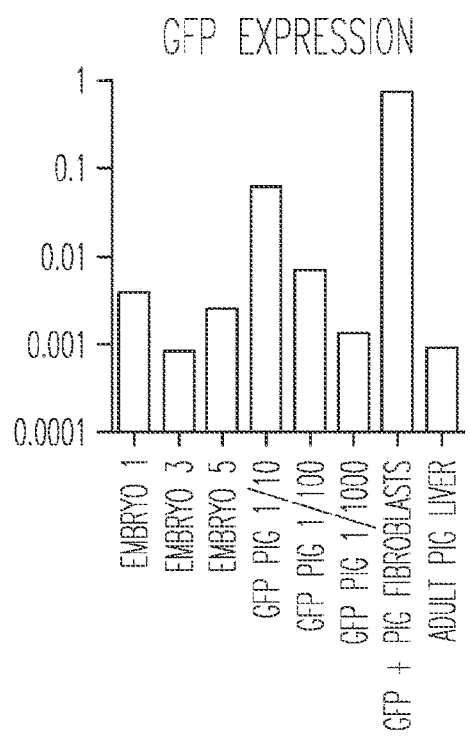
Figure 6D:
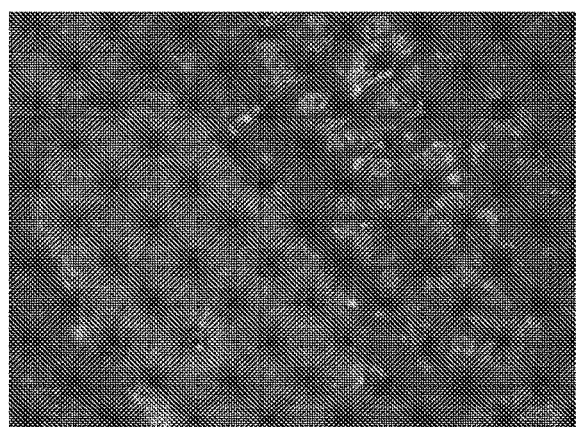

MYF5/MYOD/MRF4 null embryos were harvested and analyzed at E18.0 FIGS. 4A and 4B). In the null, myotome development is impaired and desmin is absent when compared to Wt embryos. In contrast, cardiac desmin is preserved in the null indicating the specificity of the gene edit. The results in the mouse and pig reflect a similar phenotype and support the notion that the function of MYF5/MYOD/MRF4 are conserved between mice and pigs as mutant embryos lack skeletal muscle. These data demonstrate that one can direct multiple mutations into the porcine genome to support growth of chimeric organs that will be humanized in more than one cell type.

Complementation of MYF5/MYOD/MRF4 Knockout Phenotype with GFP WT Pig Blastomeres Porcine MYF5/MYOD/MRF4 null blastocysts were generated using SCNT, and injected with GFP-labeled porcine blastomeres (since no validated porcine ES cells are available, blastomeres were utilized for this experiment). The resulting chimeras were implanted in pseudopregnant sows and examined at E20. The feasibility of complementation was demonstrated, as liver and yolk sac were GFP positive. Additionally, approximately 10% of porcine MYF5/MYOD/MRF4 null blastocysts were GFP labeled by PCR analysis. These data support the feasibility of pig:pig complementation in this porcine mutant host.

Human Induced Human Pluripotent Stem Cells (hiPSC) Integrate into the Inner Cell Mas of Porcine Parthenotes, Blastocyst and Selection of Human Stem Cell Donors Additional data are provided to demonstrate generation human-pig chimeras. The capacity of human umbilical cord stem cells (hUCBSC) and hiPSC were examined for their capacity to integrate into the porcine blastocysts and participate in embryonic development. Porcine parthenogenetic blastocysts were generated using electrical stimulation of oocytes (and are not viable beyond midgestation). Six days following activation 9-12 dye labeled hUCBSC or hiPSC were injected into the blastocoele cavity. Blastocysts were allowed to recover two days in culture and then imaged (FIG. 5). Labeled hUCBSCs and hiPSCs were observed in the inner cell mass of 90% of the porcine blastocysts (FIGS. 5A and 5B, respectively). Comparison of DiI distribution with immunohistochemistry using human nuclear antigenspecific antibody (HNA) reveals that HNA antibody detects injected human stem cells (FIG. 5A, arrows). Blastocysts injected with EdU labeled hiPSC were further pulsed with BrdU for 1 hour before harvest to detect proliferating cells Double labeling with EdU reveals that injected human stem cells continued to proliferate after 48 hrs of injection (FIG. 5B, arrows). These results demonstrate the incorporation of human stem cells into the ICM of porcine blastocysts, and the developmental progression of the chimeric blastocysts to the hatching stage in preparation for implantation into the uterus.

Novel gene editing strategies were utilized in the pig and data demonstrates that hiPSCs will participate in the developing porcine embryo (morula or blastocyst). Thus, human stem/progenitor cell populations can rescue the MYF5/MYOD/MRF4 mutant porcine embryo. Stem cells, such as hiPSCs, can be progenitors to every skeletal muscle cell in the MYF5/MYOD/MRF4 mutant pre-term embryo.

Recent studies have demonstrated that blastocyst complementation strategies using a genetically mutated host lacking a key regulatory gene has produced donor organs in the pig (1-4). TALEN-mediated techniques (21, 22) were used herein to successfully knock out MYF5/MYOD/MRF4 in the porcine embryo and the data support the notion that these mutant embryos lack myotomes and desmin (FIG. 4). Provided herein is evidence that WT-GFP labeled porcine blastomeres populated the skeletal muscle lineages of the porcine MYF5/MYOD/MRF4 null host (FIG. 6), indicating that MYF5/MYOD/MRF4 are ideal targets to generate the host for skeletal muscle complementation. The data further support the notion that human stem cells (human cord blood stem cells and human iPSCs can integrate into the ICM of porcine parthenotes (FIG. 5).

Example 2

Materials and Methods

TALEN Design and Production

Candidate TALEN target DNA sequences and RVD sequences were identified using the online tool "TAL EFFECTOR NUCLEOTIDE TARGETER 2.0". Plasmids for TALEN DNA transfections or in vitro TALEN mRNA transcription were then constructed by following the Golden Gate Assembly protocol using RCIscript-GOLDYTALEN (Addgene ID 38143) as final destination vector (Carlson 2012). Assembled RCIscript vectors prepared using the QIAPREP SPIN MINIPREP kit (Qiagen) were linearized by SacI to be used as templates for in vitro TALEN mRNA transcription using the mMESSAGE mMACHINE® T3 Kit (Ambion) as indicated previously (Carlson, 2009). Resulting mRNA was DNAse treated prior to purification using the MEGACLEAR REACTION CLEANUP kit (Applied Biosciences) or RNeasy kit, (Qiagen).

Tissue Culture and Transfection

Pig fibroblasts were maintained at 37 or 30 degrees Celsius (as indicated) at 5% CO2 in DMEM supplemented with 10% fetal bovine serum, 100 I.U./mL penicillin and streptomycin, 2 mM L-Glutamine and 10 mM Hepes. The Neon Transfection system (Life Technologies) was used to deliver TALENs and HDR oligos. Low passage Ossabaw or Landrace pig fibroblasts at 70-100% confluency were spilt 1:2 and harvested the next day at 70-80% confluency. Approximately 00,000 cells were resuspended in "R" Buffer (Life Technologies) with mRNA TALENs and HDR oligos and electroporated in 100 uL tips using the following parameters: input voltage: 1800V; pulse width: 20 ns; pulse number: 1. 0.1-4 ug of TALEN mRNA and 0.1-0.4 nmol of HDR oligos for the specific gene(s) of interest were included for each transfection. Transfected cells were cultured for 2 or 3 days at 30 degrees Celsius, and then analyzed for gene editing efficiency and plated for colonic.

Dilution Cloning

Two or three days post transfection, 50 to 250 cells were seeded onto 10 cm dishes and cultured until individual colonies reached circa 5 mm in diameter, 8 mL of a 1:4 (vol/vol) mixture of TrypLE and DMEM media (Life Technologies) was added and colonies were aspirated, transferred into wells of a 48-well dish and a replica % well dish and cultured under the same conditions. Colonies reaching confluence were collected and for cryopreservation and sample preparation for genotyping.

Sample Preparation

Transfected cell populations at day 3 and 10 were collected from a well of a 6-well dish and 10-30% were resuspended in 50 μl of 1×PCR compatible lysis buffet: 10 mM Tris-Cl pH 8.0, 2 mM EDTA, 0.45% Tryton X-100 (vol/vol), 0.45% Tween-20 (vol/vol) freshly supplemented with 200 μg/ml Proteinase K. The lysates were processed in a thermal cycler using the following program: 55° C. for 60 minutes, 95° C. for 15 minutes.

Analysis of Gene-Edits

PCR flanking the intended sites was conducted using AccuStart™ Taq DNA Polymerase HiFi (Quanta Biosciences) with 1 μl of the cell lysate according to the manufacturer's recommendations. The frequency of mutation in a population was analysed with the SURVEYOR MUTATION DETECTION Kit (Transgenomic) according to the manufacturer's recommendations using 10 μl of the PCR product as described above. SURVEYOR reactions were resolved on a 10% TBE polyacrylamide gels and visualized by ethidium bromide staining. Densitometry measurements of the bands were performed using ImageJ; and mutation rate of SURVEYOR reactions was calculated as described in (Guschin et al. 2010). Individual colonies were screened for the presence of an HDR allele using the primers ssMYOD NJ F2 to ssMYOD NJ R2 for an HDR allele in ssMYOD, ssMYF5 NJ F1 to ssMYF5 NJ R1 for an HDR allele in ssMYF5, and ssMYF6 NJ F1 to ssMYF6 NJ R1 for an HDR allele in ssMYF6. PCR products underwent restriction fragment length polymorphism analysis (RFLP) by digesting the resulting PCR amplicons with HindIII to determine whether one, both, or none of the alleles were cut and therefor contained the HDR allele. Products were resolved on agarose gels.

Swine Gene: MYOD NC_010444

Human Gene: MYOD ENSG00000129152

Frame-Shift KO Allele: It Puts a Frame-Shift and a Premature Stop Codon in Exon 1 of ssMYOD TALENs:

```
ssMYOD 1.2 (from 5' to 3')
                                         (SEQ ID NO: 1)
    Left: CAAGAGGTGCACCAC (SEQ ID NO: 2)
    Right: AGGCTGCCCAAGGTGG
``` ssMYOD 1.2 HDR Oligo
accaccaggcgggccgctgtc-
tactgtgggcctgcTAAgcttggcgtgcaaacgcaagac-
cactaacgccgacgcc gcaaggccgccac SEQ ID NO:3)
Underlined=52 bp of homology from right side of MYOD 1.2 cut site
Bold=33 bp of homology from left side of MYOD 1.2 cut site
Italicized=Inserted bases
Underlined=HindIII site
Capitalized=Premrature Termination Codon Full sequence from ssMYOD NJ F2 to ssMYOD NJ R2:
Screening Primers:

(SEQ ID NO: 4)
ssMYOD NJ F2: CGACGTAGATTTGAGGGCC (SEQ ID NO: 5)
ssMYOD NJ R2: CGCTGATTCGGGTTGCTAGA

This is the predicted PCR product when HDR occurs:

(SEQ ID NO: 6)
Cgacgtagatttgacgggccccgacggctctctctgcaactttgcaacagcggacgacttctatgatgacccgtgtttcgactc cccggacctgcgcttcttcgaggacctggacccgcgccttgtgcacgtgggcgcgctcctaaagcccgaggaacactcgca cttccctgccgcagcgcacccggccccgggagctcctgaggacgagcatgtgcgcgcgcccagcgggcaccaccaggc gggccgctgtctactgtgggcctgcTAA*gct*tggcgtgcaaacgcaagaccactaacgccgacgccgcaaggccgcc accatgcgcgagcggcgccgcttgagcaaagtcaacgaggccttcgagactctcaagcgctgcacgtctagcaacccgaat cagcg This is the predicted PCR product of the wild-type allele:

(SEQ ID NO: 7)
Cgacgtagatttgacgggccccgacggctctctctgcaactttgcaacag cggacgacttctatgatgacccgtgtttcgactccccggacctgcgcttc ttcgaggacctggacccgcgccttgtgcacgtgggcgcgctcctaaagcc cgaggaacactcgcacttccctgccgcagcgcacccggccccgggagctc ctgaggacgagcatgtgcgcgcgcccagcgggcaccaccaggcgggccgc tgtctactgtgggcctgcaaggcgtgcaaacgcaagaccactaacgccga ccgccgcaaggccgccaccatgcgcgagcggcgccgcttgagcaaagtca acgaggccttcgagactctcaagcgctgcacgtctagcaacccgaatcag cg Swine Gene: MYF5 ENSSSCG0000000937
Human Gene: MYF5 ENSG00000111049
Frame-shift KO allele: It puts a frame-shift and a premature stop codon in exon 1 of ssMYF5
TALENs:

ssMYF5 1.1 (from 5' to 3')
(SEQ ID NO: 8)
Left: GCCTCATGTGGGCCTG
(SEQ ID NO: 9)
Right: AAATCCACCACCATGG ssMYF5 1.1 HD oligo (SEQ ID NO: 17)
caccaccaggccggccactgcctcatgtgggcctgcTAA*gcttagcgt*gcaagaggaaatccaccaccatggatcggc ggaaggcggcca Underlined=42 bp of homology from right side of MYF5 1.1 cut site
Bold=43 bp of homology from left side of MYF5 1.1 cut site
Italicized=Inserted bases
Underlined=HindIII site
Capitalized=Premature Termination Codon Full sequence from ssMYF5 NJ F1 to sMYF5 NJ R1:
Screening Primers:

(SEQ ID NO: 10)
ssMYF5 NJ F1: GCCTGTCCGCAGAAGATGGA (SEQ ID NO: 11)
ssMYF5 NJ R1: TTACCATGCCGTCGGAGCAG

This is the predicted PCR product when HDR occurs:

(SEQ ID NO: 12)
gcctgtccgcagaagatggacctgatggacggctgccagttctcgccttctgagtacttctacgatggctcctgcatcccatccc
ccgagggcgagttcggggacgagtttgagccacgagtggctgctttcggggcgcacaaagcagacctgcccggctcagac
gaggaagagcacgtgcgagcacctacgggccaccaccaggccggccactgcctcatgtgggcctgcTAA*gctt*ag*cg*
*t*gcaagaggaaatccaccaccatggatcggcggaaggcggccaccatgcgcgagcggagacgcctgaagaaggtcaacc
aggcgtttgagacgctcaagaggtgcaccacgactaaccccaaccagaggctgcccaaggtggagatcctcaggaatgcca
tccgctacattgagagcctgcaggagctgctgagggagcaggtggaaaactactacagcctgcccaggcagagctgctctg
agcccaccagccccacctccagctgctccgacggcatggtaa This is the predicted PCR product of the wild-type allele:

(SEQ ID NO: 13)
Gcctgtccgcagaagatggacctgatggacggctgccagttctcgccttc
tgagtacttctacgatggctcctgcatcccatccccgagggcgagttcg
gggacgagtttgagccacgagtggctgctttcggggcgcacaaagcagac
ctgcccggctcagacgaggaagagcacgtgcgagcacctacgggccacca
ccaggccggccactgcctcatgtgggcctgcaaagcgtgcaagaggaaat
ccaccaccatggatcggcggaaggcggccaccatgcgcgagcggagacgc
ctgaagaaggtcaaccaggcgtttgagacgctcaagaggtgcaccacgac
taaccccaaccagaggctgcccaaggtggagatcctcaggaatgccatcc
gctacattgagagcctgcaggagctgctgagggagcaggtggaaaactac
tacagcctgcccaggcagagctgctctgagcccaccagccccacctccag
ctgctccgacggcatggtaa Swine Gene: MYF6 ENSSSCG00000026533 (also known as MRF4)
Human Gene: MYF6 ENSG00000111046
Frame-shift KO allele: It puts a frame-shift and a premature stop codon in exon 1 of ssMYF6
TALENs:

ssMYF6 1.2 (from 5' to 3')
(SEQ ID NO: 14)
Left: GCCAGGACCAAATGCC (SEQ ID NO: 15)
Right: GACAGCAGTGGAGAGGA ssMYF6 1.2 HDR Oligo (SEQ ID NO: 16)
ccagggagtgatggtaccctgtccccTAA*gctt*caggaccaaatgccccggaagctgggagcgacagcagtgga
gaggaacatgtcct Underlined=32 bp of homology from right side of MYF6 1.2 cut site
Bold=54 bp of homology from left side of MYF6 1.2 cut site
Italicized=Inserted bases
Underlined=HindIII site
Capitalized=Premature Termination Codon
Full Sequence from ssMYF6 NJ F1 to ssMYF6 NJ R1:
Screening Primers:

(SEQ ID NO: 18)
ssMYF6 NJ F1: ATCTGGGTGGCTCCTCTGGGTT (SEQ ID NO: 19)
ssMYF6 NJ R1: TAGTTGATGGCGCTCCGCAG

This is the predicted PCR product when HDR occurs:

(SEQ ID NO: 20)

Atctgggtggctcctctgggttttgagcccatcacccagttcagaccgagtcagaggccaaggaggagaacatgatgatgg accttttttgaaactggctcctatttcttctatttggacggggaaaatgttaccctgcagcccctagaagtggcagaaggctctcctt tgtatccagggagtgatggtaccctgtcccccT*AA*gct tcaggaccaaatgccccggaagctgggagcgacagcagt ggagaggaacatgtcctggcgccccaggcctgcagcctccccactgccccggccaatgtctgatctgggcttgcaagacct gcaagagaaatctgccccaaccgaccgcaggaaggcggccactctgcgcgagaggaggcggctgaagaaaatcaacg aggccttcgaggcactgaagcggcggactgtggccaaccccaaccaaaggctgcccaaggtggagatcctgcggagcgc catcaacta This is the predicted PCR product of the wild-type allele:

(SEQ ID NO: 21)
Atctgggtggctcctctgggttttgagcccatcacccagttcagaccga gtcagaggccaaggaggagaacatgatgatggaccttttgaaactggct cctatttcttctatttggacggggaaaatgttaccctgcagcccctagaa gtggcagaaggctctcctttgtatccagggagtgatggtaccctgtcccc ctgccaggaccaaatgccccggaagctgggagcgacagcagtggagagg aacatgtcctggcgccccaggcctgcagcctccccactgccccggccaa tgtctgatctgggcttgcaagacctgcaagagaaatctgccccaaccga ccgcaggaaggcggccactctgcgcgagaggaggcggctgaagaaaatca acgaggccttcgaggcactgaagcggcggactgtggccaaccccaaccaa aggctgcccaaggtggagatcctgcggagcgccatcaacta

BIBLIOGRAPHY

1. Kobayashi T, et al. Cell. 2010; 142(5):787-799.
2. Usui J, et al. Am J Pathol. 2012; 180(6):2417-2426.
3. Bort R, et al. Dev Biol. 2006; 290(1):44-56.
4. Matsunari H, et al. Proc Natl Acad Sci USA. 2013; 110(12):4557-4562.
5. Woolf A D, Pileger B. Bulletin of the World Health Organization. 2003; 81(9):646-656
6. Saourin L A, Rudnicki M A, Clin Genet. 2000; 57:16-25.
7. Tapscott S J. Development. 2005; 132:2685-2695.
8. Kassar-Duchossoy L, et al. Nature. 2004; 431:466-471.
9. Shi X, Garry D J. Genes Dev. 2006; 20:1692-1708.
10. Berkes C A, Tapscott S J. Semin Cell Dev Biol. 2005; 16:585-595.
11. Jansen K M, Pavlath G K. Methods Mol Biol. 2008; 475:115-133.
12. Pasut A, et al. Methods Mol Biol. 2012; 798:53-64.
13. Lewis F C, Henning B J, et al. Stem Cells Transl Med. 2014; 3(6):702-712.
14. Te Pas M F, et al. BMC Dev Biol. 2007; 7:66.
15. Kure-bayashi S, et al. Theriogeology. 2000; 53(5):1105-1119.
16. Zhu J, et al. Cloning Stem Cells. 2003; 5(4):355-365.
17. King T J, et al. Reproduction. 2002; 123(4):507-515.
18. Nakano K, et al. PLoS One. 2013; 84):e61900.
1. Zhu J, et al. Cloning Stem Cells. 2003; 5(4):355-365.
20. Takeda K, et al. Mitochondrion. 2010; 10(2):137-142.
21. Carlson D F, et al. Proc Nat Acad Sci USA. 2012; 109(43):17382-17387.
22. Tan W, et al. Proc Natl Acad Sci USA. 2013; 110(41): 16526-16531.
23. Grefte S, et al. Eur J Oral Sci. 2012; 120(1):38-45.

All publications, patents, and patent applications, Genbank sequences, websites and other published materials referred to throughout the disclosure herein are herein incorporated by reference to the same extent as if each individual publication, patent, or patent application. Genbank sequences, websites and other published materials was specifically and individually indicated to be incorporated by reference. In the event that the definition of a term incorporated by reference conflicts with a term defined herein, this specification shall control.

What is claimed is:

1. A method for producing a chimeric pig embryo comprising:
    a) generating a porcine cell with a homozygous disruption of MYF5, MYOD, and MYF6 genes in its genome, wherein the cell is not capable of expressing MYF5 gene, MYOD gene, and MYF6 gene;
    b) introducing the cell of a) into an enucleated pig oocyte to produce a pig embryo;
    c) culturing the pig embryo of b) to the morula or blastocyst stage; and
    d) introducing human pluripotent stem cells into the inner mass cells of the morula or blastocyst of c),
    wherein the human pluripotent stem cells comprise intact human MYF5 genes, MYOD genes, and MYF6 genes in its genome.

2. The method of claim 1, wherein the pluripotent stem cell is an induced pluripotent stem cell.

3. The method of claim 2, wherein the induced pluripotent cell is formed from a fibroblast cell.

* * * * *

UNITED STATES PATENT AND TRADEMARK OFFICE
CERTIFICATE OF CORRECTION

| | |
|---|---|
| PATENT NO. | : 12,089,574 B2 |
| APPLICATION NO. | : 16/952807 |
| DATED | : September 17, 2024 |
| INVENTOR(S) | : Garry et al. |

It is certified that error appears in the above-identified patent and that said Letters Patent is hereby corrected as shown below:

On the Title Page

On page 3, in Column 1, Item (56) under "Other Publications", Line 27, delete "liverstock"," and insert --livestock",-- therefor On page 3, in Column 2, Item (56) under "Other Publications", Line 31, delete ""Myogenesls" and insert --"Myogenesis-- therefor On page 4, in Column 1, Item (56) under "Other Publications", Line 9, delete "CAMP-responsive" and insert --cAMP-responsive-- therefor On page 4, in Column 1, Item (56) under "Other Publications", Line 31, delete "microarry" and insert --microarray-- therefor In the Specification In Column 1, Line 57, delete "of" and insert --or-- therefor In Column 2, Line 27, after "comprising", insert --:--

In Column 2, Line 34, delete "(r" and insert --or-- therefor

In Column 2, Line 40, delete "stein" and insert --stem-- therefor

In Column 2, Line 43, delete "cl" and insert --c)-- therefor

In Column 2, Line 49, delete "mill" and insert --null-- therefor

In Column 2, Line 64, delete "b)," and insert --b);-- therefor

Signed and Sealed this
Third Day of December, 2024

*Katherine Kelly Vidal*
Katherine Kelly Vidal
*Director of the United States Patent and Trademark Office*

CERTIFICATE OF CORRECTION (continued)
U.S. Pat. No. 12,089,574 B2

In Column 2, Line 64, delete "c" and insert --c)-- therefor

In Column 3, Line 29, delete "at" and insert --a)-- therefor

In Column 3, Line 41, after "blastocyst", insert --;--

In Column 3, Line 42, delete "stein" and insert --stem-- therefor

In Column 3, Line 43, delete "Or" and insert --or-- therefor

In Column 4, Line 13, delete "ENSSSCG00000937" and insert --ENSSSCG00000000937-- therefor In Column 4, Line 15, delete "ENSG00000124152)," and insert --ENSG00000129152),-- therefor In Column 4, Line 16, delete "ENSSSCG0000026533" and insert --ENSSSCG00000026533-- therefor In Column 4, Line 33, delete "20151/168125," and insert --2015/168125,-- therefor In Column 4, Line 46, delete "muster" and insert --master-- therefor In Column 5, Line 45, delete "GP-labeled" and insert --GFP-labeled-- therefor In Column 6, Line 46, delete "ems," and insert --items,-- therefor In Column 6, Line 53, delete "bit" and insert --but-- therefor In Column 8, Line 15, delete "stein" and insert --stem-- therefor In Column 8, Line 31, delete "stein" and insert --stem-- therefor In Column 9, Line 14, delete "adminstered" and insert --administered-- therefor In Column 9, Line 53, delete "positon" and insert --position-- therefor In Column 10, Line 23, delete "10.0." and insert --10.0,-- therefor In Column 10, Line 34, delete "NB LAST)" and insert --NBLAST)-- therefor In Column 11, Line 3, delete "phosphorthioate," and insert --phosphorothioate,-- therefor In Column 11, Line 7, delete "live" and insert --five-- therefor In Column 11, Line 37, delete ""U"replaces"."" and insert --"U" replaces "T."-- therefor In Column 12, Line 3, delete "linger" and insert --finger-- therefor In Column 12, Line 34, delete "(pseudopragnant/surrogate)" and insert --(pseudopregnant/surrogate)-- therefor In Column 12, Line 58, after "organism", insert --,--

In Column 12, Line 61, after "product", insert --.--

In Column 13, Line 26, delete "refer" and insert --refers-- therefor

In Column 13, Line 33, delete "95c" and insert --95%-- therefor

In Column 14, Line 40, delete "Letts," and insert --Letts.-- therefor

In Column 14, Line 42, delete "term "comprises"" and insert --terms "comprises,"-- therefor In Column 15, Line 10, delete "xenogeneic" and insert --xenogenic-- therefor In Column 15, Line 16, delete "give" and insert --gave-- therefor In Column 15, Line 47, delete "m" and insert --in-- therefor In Column 15, Line 64, delete "cortosteroids," and insert --corticosteroids,-- therefor In Column 16, Line 38, delete "myopathy." and insert --myopathy,-- therefor In Column 16, Line 38, delete "myopathy." and insert --myopathy,-- therefor In Column 16, Lines 46-47, delete "myoglohinurias." and insert --myoglobinurias.-- therefor In Column 16, Line 48, delete "MYF5/MYOD/NRF4" and insert --MYF5/MYOD/MRF4-- therefor In Column 17, Line 5, delete "127," and insert --(27,-- therefor In Column 17, Line 30, delete "alter" and insert --after-- therefor In Column 17, Line 32, delete "alter" and insert --after-- therefor In Column 17, Line 44, after "following", insert --:--

In Column 17, Line 45, delete "1" and insert --(1-- therefor

In Column 17, Line 46, delete "mg/kg," and insert --mg/kg;-- therefor

In Column 17, Line 48, delete "45%" and insert --(5%-- therefor

In Column 17, Line 60, delete "Ltd." and insert --Ltd,-- therefor

CERTIFICATE OF CORRECTION (continued)
U.S. Pat. No. 12,089,574 B2

In Column 18, Line 2, after "Myf5", insert --,--

In Column 18, Line 9, delete "10)," and insert --10).-- therefor

In Column 18, Line 52, delete "Mas" and insert --Mass-- therefor

In Column 19, Line 4, after "cells", insert --.--

In Column 19, Line 32, after "iPSCs", insert --)--

In Column 19, Line 43, delete "transfections" and insert --transfection-- therefor In Column 19, Line 65, delete "00,000" and insert --600,000-- therefor In Column 20, Line 1, delete "ns;" and insert --ms;-- therefor In Column 20, Line 3, delete "genets)" and insert --gene(s)-- therefor In Column 20, Line 6, delete "colonic." and insert --colonics.-- therefor In Column 20, Line 11, delete "diameter," and insert --diameter.-- therefor In Column 20, Line 14, delete ""%"" and insert --96-- therefor In Column 20, Line 22, delete "buffet:" and insert --buffer:-- therefor In Column 20, Line 31, delete "Tag" and insert --Taq-- therefor In Column 21, Line 11, delete "Capitalized=Premrature" and insert --Capitalized=Premature-- therefor In Column 22, Line 6, delete "CGACGTAGATTTGAGGGCC" and insert --CGACGTAGATTTGACGGGCC-- therefor In Column 22, Line 46, delete "ENSSSCG0000000937" and insert --ENSSSCG00000000937-- therefor In Column 22, Line 58, delete "HD" and insert --HDR-- therefor In Column 24, Line 1, delete "sMYF5" and insert --ssMYF5-- therefor In Column 26, Line 3, delete "Pileger" and insert --Pfleger-- therefor In Column 26, Line 5, delete "Saourin" and insert --Sabourin-- therefor In Column 26, Line 40 (Approx.), delete "Theriogeology." and insert --Theriogenology.-- therefor
In Column 26, Line 46 (Approx.), delete "84):e61900." and insert --8(4):e61900.-- therefor

CERTIFICATE OF CORRECTION (continued)
U.S. Pat. No. 12,089,574 B2

In Column 26, Line 48 (Approx.), delete "1." and insert --19.-- therefor

In Column 26, Line 50 (Approx.), delete "Nat" and insert --Natl-- therefor

In Column 26, Line 62, delete "application." and insert --application,-- therefor

SEQUENCE LISTING

```
<160> NUMBER OF SEQ ID NOS: 25

<210> SEQ ID NO 1
<211> LENGTH: 15
<212> TYPE: DNA
<213> ORGANISM: Artificial Sequence
<220> FEATURE:
<223> OTHER INFORMATION: A synthetic oligonucleotide

<400> SEQUENCE: 1
caagaggtgc accac                                                        15

<210> SEQ ID NO 2
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 2
aggctgccca aggtgg                                                       16

<210> SEQ ID NO 3
<211> LENGTH: 90
<212> TYPE: DNA
<213> ORGANISM: Artificial Sequence
<220> FEATURE:
<223> OTHER INFORMATION: A synthetic oligonucleotide

<400> SEQUENCE: 3
accaccaggc gggccgctgt ctactgtggg cctgctaagc ttggcgtgca aacgcaagac       60
cactaacgcc gaccgccgca aggccgccac                                        90

<210> SEQ ID NO 4
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 4
cgacgtagat ttgacgggcc                                                   20

<210> SEQ ID NO 5
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 5
cgctgattcg ggttgctaga                                                   20

<210> SEQ ID NO 6
<211> LENGTH: 407
<212> TYPE: DNA
<213> ORGANISM: Artificial Sequence
<220> FEATURE:
<223> OTHER INFORMATION: A synthetic oligonucleotide

<400> SEQUENCE: 6
cgacgtagat ttgacgggcc ccgacggctc tctctgcaac tttgcaacag cggacgactt       60
ctatgatgac ccgtgtttcg actccccgga cctgcgcttc ttcgaggacc tggacccgcg     120
ccttgtgcac gtgggcgcgc tcctaaagcc cgaggaacac tcgcacttcc ctgccgcagc     180
```
gcacccggcc ccgggagctc ctgaggacga gcatgtgcgc gcgcccagcg ggcaccacca    240
ggcgggccgc tgtctactgt gggcctgcta agcttggcgt gcaaacgcaa gaccactaac    300
gccgaccgcc gcaaggccgc caccatgcgc gagcggcgcc gcttgagcaa agtcaacgag    360
gccttcgaga ctctcaagcg ctgcacgtct agcaacccga atcagcg                  407

<210> SEQ ID NO 7
<211> LENGTH: 402
<212> TYPE: DNA
<213> ORGANISM: Artificial Sequence
<220> FEATURE:
<223> OTHER INFORMATION: A synthetic oligonucleotide

<400> SEQUENCE: 7
cgacgtagat ttgacgggcc ccgacggctc tctctgcaac tttgcaacag cggacgactt     60
ctatgatgac ccgtgtttcg actccccgga cctgcgcttc ttcgaggacc tggacccgcg    120
ccttgtgcac gtgggcgcgc tcctaaagcc cgaggaacac tcgcacttcc ctgccgcagc    180
gcacccggcc ccgggagctc ctgaggacga gcatgtgcgc gcgcccagcg ggcaccacca    240
ggcgggccgc tgtctactgt gggcctgcaa ggcgtgcaaa cgcaagacca ctaacgccga    300
ccgccgcaag gccgccacca tgcgcgagcg cgccgcttg agcaaagtca acgaggcctt    360
cgagactctc aagcgctgca cgtctagcaa cccgaatcag cg                       402

<210> SEQ ID NO 8
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 8
gcctcatgtg ggcctg                                                     16

<210> SEQ ID NO 9
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 9
aaatccacca ccatgg                                                     16

<210> SEQ ID NO 10
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 10
gcctgtccgc agaagatgga                                                 20

<210> SEQ ID NO 11
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 11
ttaccatgcc gtcggagcag                                                    20

<210> SEQ ID NO 12
<211> LENGTH: 525
<212> TYPE: DNA
<213> ORGANISM: Artificial Sequence
<220> FEATURE:
<223> OTHER INFORMATION: A synthetic oligonucleotide

<400> SEQUENCE: 12
gcctgtccgc agaagatgga cctgatggac ggctgccagt tctcgccttc tgagtacttc      60
tacgatggct cctgcatccc atcccccgag ggcgagttcg gggacgagtt tgagccacga     120
gtggctgctt tcggggcgca caaagcagac ctgcccggct cagacgagga agagcacgtg     180
cgagcaccta cgggccacca ccaggccggc cactgcctca tgtgggcctg ctaagcttag     240
cgtgcaagag gaaatccacc accatggatc ggcggaaggc ggccaccatg cgcgagcgga     300
gacgcctgaa gaaggtcaac caggcgtttg agacgctcaa gaggtgcacc acgactaacc     360
ccaaccagag gctgcccaag gtggagatcc tcaggaatgc catccgctac attgagagcc     420
tgcaggagct gctgagggag caggtggaaa actactacag cctgcccagg cagagctgct     480
ctgagcccac cagccccacc tccagctgct ccgacggcat ggtaa                     525

<210> SEQ ID NO 13
<211> LENGTH: 520
<212> TYPE: DNA
<213> ORGANISM: Artificial Sequence
<220> FEATURE:
<223> OTHER INFORMATION: A synthetic oligonucleotide

<400> SEQUENCE: 13
gcctgtccgc agaagatgga cctgatggac ggctgccagt tctcgccttc tgagtacttc      60
tacgatggct cctgcatccc atcccccgag ggcgagttcg gggacgagtt tgagccacga     120
gtggctgctt tcggggcgca caaagcagac ctgcccggct cagacgagga agagcacgtg     180
cgagcaccta cgggccacca ccaggccggc cactgcctca tgtgggcctg caaagcgtgc     240
aagaggaaat ccaccaccat ggatcggcgg aaggcggcca ccatgcgcga gcggagacgc     300
ctgaagaagg tcaaccaggc gtttgagacg ctcaagaggt gcaccacgac taaccccaac     360
cagaggctgc ccaaggtgga gatcctcagg aatgccatcc gctacattga gagcctgcag     420
gagctgctga gggagcaggt ggaaaactac tacagcctgc ccaggcagag ctgctctgag     480
cccaccagcc ccacctccag ctgctccgac ggcatggtaa                           520

<210> SEQ ID NO 14
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 14
gccaggacca aatgcc                                                        16

<210> SEQ ID NO 15
<211> LENGTH: 17
<212> TYPE: DNA
<213> ORGANISM: Artificial Sequence
<220> FEATURE:

<223> OTHER INFORMATION: A synthetic oligonucleotide

<400> SEQUENCE: 15
gacagcagtg gagagga                                                          17

<210> SEQ ID NO 16
<211> LENGTH: 90
<212> TYPE: DNA
<213> ORGANISM: Artificial Sequence
<220> FEATURE:
<223> OTHER INFORMATION: A synthetic oligonucleotide

<400> SEQUENCE: 16
ccagggagtg atggtaccct gtcccctaa gcttcaggac caaatgcccc cggaagctgg            60
gagcgacagc agtggagagg aacatgtcct                                            90

<210> SEQ ID NO 17
<211> LENGTH: 90
<212> TYPE: DNA
<213> ORGANISM: Artificial Sequence
<220> FEATURE:
<223> OTHER INFORMATION: A synthetic oligonucleotide

<400> SEQUENCE: 17
caccaccagg ccggccactg cctcatgtgg gcctgctaag cttagcgtgc aagaggaaat           60
ccaccaccat ggatcggcgg aaggcggcca                                            90

<210> SEQ ID NO 18
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 18
atctgggtgg ctcctctggg tt                                                    22

<210> SEQ ID NO 19
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 19
tagttgatgg cgctccgcag                                                       20

<210> SEQ ID NO 20
<211> LENGTH: 495
<212> TYPE: DNA
<213> ORGANISM: Artificial Sequence
<220> FEATURE:
<223> OTHER INFORMATION: A synthetic oligonucleotide

<400> SEQUENCE: 20
atctgggtgg ctcctctggg tttttgagcc catcacccag ttcagaccga gtcagaggcc           60
aaggaggaga acatgatgat ggacctttttt gaaactggct cctatttctt ctatttggac         120
ggggaaaatg ttaccctgca gccctagaa gtggcagaag gctctccttt gtatccaggg          180
agtgatggta ccctgtcccc ctaagcttca ggaccaaatg ccccggaag ctgggagcga          240 cagcagtgga ggaacatg tcctggcgcc cccaggcctg cagcctcccc actgccccgg           300
ccaatgtctg atctgggctt gcaagacctg caagagaaaa tctgccccaa ccgaccgcag         360

```
gaaggcggcc actctgcgcg agaggaggcg gctgaagaaa atcaacgagg ccttcgaggc    420
actgaagcgg cggactgtgg ccaaccccaa ccaaaggctg cccaaggtgg agatcctgcg    480
gagcgccatc aacta                                                    495
```

<210> SEQ ID NO 21
<211> LENGTH: 491
<212> TYPE: DNA
<213> ORGANISM: Artificial Sequence
<220> FEATURE:
<223> OTHER INFORMATION: A synthetic oligonucleotide

<400> SEQUENCE: 21

```
atctgggtgg ctcctctggg tttttgagcc catcacccag ttcagaccga gtcagaggcc    60
aaggaggaga acatgatgat ggacctttt gaaactggct cctatttctt ctatttggac    120
ggggaaaatg ttaccctgca gcccctagaa gtggcagaag gctctccttt gtatccaggg    180
agtgatggta ccctgtcccc ctgccaggac caaatgcccc cggaagctgg gagcgacagc    240
agtggagagg aacatgtcct ggcgccccca ggcctgcagc ctccccactg ccccggccaa    300
tgtctgatct gggcttgcaa gacctgcaag agaaaatctg ccccaaccga ccgcaggaag    360
gcggccactc tgcgcgagag gaggcggctg aagaaaatca cgaggccctt cgaggcactg    420
aagcggcgga ctgtgccaa ccccaaccaa aggctgccca aggtggagat cctgcggagc    480
gccatcaact a                                                        491
```

<210> SEQ ID NO 22
<211> LENGTH: 61
<212> TYPE: DNA
<213> ORGANISM: Artificial Sequence
<220> FEATURE:
<223> OTHER INFORMATION: A synthetic oligonucleotide

<400> SEQUENCE: 22

```
gccgctgtct acttgtgggc ctgcaaggcg tgcaaacgca agaccactaa cgccgaccgc    60
c                                                                   61
```

<210> SEQ ID NO 23
<211> LENGTH: 60
<212> TYPE: DNA
<213> ORGANISM: Artificial Sequence
<220> FEATURE:
<223> OTHER INFORMATION: A synthetic oligonucleotide

<400> SEQUENCE: 23

```
gccactgcct catgtgggcc tgcaaagcgt gcaagaggaa atccaccacc atggatcggc    60
```

<210> SEQ ID NO 24
<211> LENGTH: 59
<212> TYPE: DNA
<213> ORGANISM: Artificial Sequence
<220> FEATURE:
<223> OTHER INFORMATION: A synthetic oligonucleotide

<400> SEQUENCE: 24

```
cccctgccag gaccaaatgc ccccggaagc tgggagcgac agcagtggag aggaacatg     59
```

<210> SEQ ID NO 25
<211> LENGTH: 60
<212> TYPE: DNA
<213> ORGANISM: Artificial Sequence
<220> FEATURE:

```
<223> OTHER INFORMATION: A synthetic oligonucleotide

<400> SEQUENCE: 25
gccgctgtct actgtgggcc tgcaaggcgt gcaaacgcaa gaccactaac gccgaccgcc    60
```